(12) United States Patent
Ang et al.

(10) Patent No.: US 11,484,242 B2
(45) Date of Patent: Nov. 1, 2022

(54) DETECTING AND USING BODY TISSUE ELECTRICAL SIGNALS

(71) Applicant: Pison Technology, Inc., Brookline, MA (US)

(72) Inventors: Dexter W. Ang, Brookline, MA (US); David O Cipoletta, Chepachet, RI (US); Samuel J. Karnes, Narragansett, RI (US); Michael P. Kowalczyk, Newport, RI (US); Sidhant Srikumar, Brookline, MA (US)

(73) Assignee: Pison Technology, Inc., Boston, MA (US)

( * ) Notice: Subject to any disclaimer, the term of this patent is extended or adjusted under 35 U.S.C. 154(b) by 1110 days.

(21) Appl. No.: 16/104,273

(22) Filed: Aug. 17, 2018

(65) Prior Publication Data

US 2019/0082996 A1 Mar. 21, 2019

Related U.S. Application Data

(63) Continuation of application No. 15/826,131, filed on Nov. 29, 2017, now Pat. No. 10,070,799.

(Continued)

(51) Int. Cl.
*A61B 5/00* (2006.01)
*A61B 5/24* (2021.01)
(Continued)

(52) U.S. Cl.
CPC ............ *A61B 5/389* (2021.01); *A61B 5/053* (2013.01); *A61B 5/24* (2021.01); *G06F 1/163* (2013.01);
(Continued)

(58) Field of Classification Search
CPC ... A61B 5/0488; A61B 5/04888; A61B 5/681; A61B 5/6824; A61B 5/7267;
(Continued)

(56) References Cited

U.S. PATENT DOCUMENTS 5,217,014 A 6/1993 Han et al.
5,287,859 A 2/1994 John
(Continued)

FOREIGN PATENT DOCUMENTS

CN 101963866 2/2011
KR 10-2016-0126660 11/2016
(Continued)

OTHER PUBLICATIONS

Chinese Office Action in Chinese Application No. 201780060545.3, dated Nov. 7, 2019, 18 pages with English Translation.
(Continued)

*Primary Examiner* — Eun Hwa Kim
(74) *Attorney, Agent, or Firm* — Scale LLP

(57) ABSTRACT

Bio-potentials are sensed on the skin of a subject. The bio-potentials include muscle bio-potentials, and nerve bio-potentials. Skin sensors are positioned to enable the sensing circuitry to emphasize the nerve bio-potentials and deemphasize the muscle bio-potentials in processed bio-potential signals generated by the sensing circuitry. A machine learning component identifies control sequences or tracks body motions based on the processed bio-potential signals.

14 Claims, 19 Drawing Sheets

Related U.S. Application Data

(60) Provisional application No. 62/566,674, filed on Oct. 2, 2017, provisional application No. 62/429,334, filed on Dec. 2, 2016.

(51) Int. Cl.

| | | |
|---|---|---|
| *G06F 3/023* | (2006.01) | |
| *A61B 5/389* | (2021.01) | |
| *G06F 1/16* | (2006.01) | |
| *A61B 5/053* | (2021.01) | |
| *G06F 3/01* | (2006.01) | |
| *A61B 5/11* | (2006.01) | |
| *A61B 5/25* | (2021.01) | |
| *A61B 5/024* | (2006.01) | |
| *A61B 5/0245* | (2006.01) | |

(52) U.S. Cl.
CPC .......... *G06F 3/015* (2013.01); *G06F 3/0236* (2013.01); *A61B 5/0024* (2013.01); *A61B 5/0245* (2013.01); *A61B 5/02438* (2013.01); *A61B 5/1114* (2013.01); *A61B 5/25* (2021.01); *A61B 5/4836* (2013.01); *A61B 5/681* (2013.01); *A61B 5/6824* (2013.01); *A61B 5/6829* (2013.01); *A61B 5/7264* (2013.01); *A61B 5/742* (2013.01); *A61B 5/7475* (2013.01); *A61B 2560/0242* (2013.01)

(58) Field of Classification Search
CPC ....... A61B 5/7278; A61B 5/013; G06F 3/015; G06F 3/017; A61F 2/72; A61F 5/013; A61H 2230/08; G06N 99/005; G06N 5/00

See application file for complete search history.

(56) References Cited

U.S. PATENT DOCUMENTS

| | | | |
|---|---|---|---|
| 5,660,177 A | 8/1997 | Faupel et al. | |
| 5,823,957 A | 10/1998 | Faupel et al. | |
| 6,244,873 B1 | 6/2001 | Hill | |
| 6,470,893 B1 | 10/2002 | Boesen | |
| 6,720,984 B1 | 4/2004 | Jorgensen et al. | |
| 7,206,625 B2 | 4/2007 | Kurtz et al. | |
| 7,333,090 B2 | 2/2008 | Tanaka et al. | |
| 7,596,393 B2 | 9/2009 | Jung et al. | |
| 8,170,656 B2 | 5/2012 | Tan et al. | |
| 8,386,026 B2 | 2/2013 | Fink et al. | |
| 8,444,559 B2 | 5/2013 | Fink et al. | |
| 8,447,704 B2 * | 5/2013 | Tan .......................... | G06F 3/017 706/62 |
| 8,694,084 B2 | 4/2014 | Sullivan et al. | |
| 8,798,710 B2 | 8/2014 | Chi | |
| 8,892,479 B2 | 11/2014 | Tan et al. | |
| 9,071,209 B1 | 6/2015 | Harrison | |
| 9,092,664 B2 | 7/2015 | Forutanpour et al. | |
| 9,170,674 B2 | 10/2015 | Forutanpour et al. | |
| 9,184,722 B2 | 11/2015 | Bakalski | |
| 9,278,453 B2 | 3/2016 | Assad | |
| 9,299,248 B2 * | 3/2016 | Lake ...................... | G06F 3/011 |
| 9,306,534 B2 | 4/2016 | Chung | |
| 9,330,666 B2 | 5/2016 | Alameh et al. | |
| 9,351,653 B1 | 5/2016 | Harrison | |
| 9,372,535 B2 | 6/2016 | Bailey et al. | |
| 9,452,287 B2 | 9/2016 | Rosenbluth | |
| 9,483,123 B2 * | 11/2016 | Aleem ..................... | G06F 3/014 |
| 9,545,221 B2 | 1/2017 | Adhikari et al. | |
| 9,545,567 B2 | 1/2017 | Han et al. | |
| 9,600,030 B2 * | 3/2017 | Bailey .................. | A61B 5/6831 |
| 9,720,515 B2 | 8/2017 | Wagner | |
| 10,070,799 B2 | 9/2018 | Ang et al. | |
| 2005/0215916 A1 | 9/2005 | Fadem et al. | |
| 2009/0326406 A1 | 12/2009 | Tan et al. | |
| 2010/0106044 A1 | 4/2010 | Linderman | |
| 2011/0251512 A1 | 10/2011 | Fink | |
| 2011/0282231 A1 | 11/2011 | Pradeep et al. | |
| 2011/0301488 A1 | 12/2011 | Schuette | |
| 2011/0306859 A1 | 12/2011 | Saldivar et al. | |
| 2012/0029399 A1 | 2/2012 | Sankai | |
| 2012/0188158 A1 | 7/2012 | Tan et al. | |
| 2013/0317648 A1 * | 11/2013 | Assad ..................... | A61B 5/389 700/258 |
| 2014/0198034 A1 | 7/2014 | Bailey et al. | |
| 2014/0210745 A1 | 7/2014 | Chizeck | |
| 2014/0240223 A1 | 8/2014 | Lake et al. | |
| 2014/0249397 A1 | 9/2014 | Lake et al. | |
| 2014/0257129 A1 * | 9/2014 | Choi ..................... | A61B 5/7225 600/546 |
| 2014/0275823 A1 | 9/2014 | Lane et al. | |
| 2015/0182160 A1 * | 7/2015 | Kim ..................... | A61B 5/7475 600/301 |
| 2015/0185853 A1 | 7/2015 | Clausen et al. | |
| 2015/0324000 A1 | 11/2015 | Park et al. | |
| 2016/0062320 A1 | 3/2016 | Chung | |
| 2016/0239128 A1 | 8/2016 | Zhang et al. | |
| 2016/0313801 A1 * | 10/2016 | Wagner .................. | G06F 1/163 |
| 2016/0366590 A1 | 12/2016 | Jun et al. | |
| 2017/0134086 A1 * | 5/2017 | Liu ..................... | H04B 7/18502 |
| 2018/0153430 A1 | 6/2018 | Ang et al. | |

FOREIGN PATENT DOCUMENTS

| | | |
|---|---|---|
| WO | WO 2001/13778 | 3/2001 |
| WO | WO 2018/102429 | 6/2018 |

OTHER PUBLICATIONS

Invitation to Pay Additional Fees, and, Where Applicable, Protest Fee in International Application No. PCT/US2017/63738, dated May 23, 2018, 2 pages.
Korean Office Action in Korean Application No. 10-2019-7004562, dated May 20, 2019, 11 pages.
PCT International Preliminary Report on Patentability in International Appln. No. PCT/US2017/063738, dated Jun. 13, 2019, 7 pages.
Chinese Office Action in Chinese Application No. 201780060545.3, dated May 8, 2020, 18 pages with English translation.
Extended European Search Report in EP Application No. 17875196. 2, dated May 29, 2020, 7 pages.
Weiguo et al., "Digital Identification Method for Pipeline Leak and Interference Signal", College of Information Science and Technology, 2014, 35(6): 1197-1203.
Korean Office Action in KR Appln. No. 10-2019-7031346, dated Dec. 24, 2020, 8 pages with English Translation.
http://www.cognionics.com/index.php/products/sensors/drypad, Nov. 27, 2017 (1 page).
Levy, Steven, "Brain-Machine Interface Isn't Sci-Fi Anymore", Sep. 13, 2017, WIRED Magazine (26 pages).
International Search Report and Written Opinion from corresponding PCT application PCT/US2017/063738 dated Jul. 19, 2018 (16 pages).
Transaction history of U.S. Appl. No. 62/566,674, filed Oct. 2, 2017.
U.S. Appl. No. 62/429,334, filed Dec. 2, 2016.

* cited by examiner

DETECTING AND USING BODY TISSUE ELECTRICAL SIGNALS

This application is a continuation application of and claims priority to U.S. nonprovisional application Ser. No. 15/826,131, filed on Nov. 29, 2017, which is entitled to the benefit of the filing date of U.S. provisional application Ser. No. 62/429,334, filed on Dec. 2, 2016, and U.S. provisional application Ser. No. 62/566,674, filed on Oct. 2, 2017, the entire contents of both of which are incorporated here by reference.

BACKGROUND

This description relates to detecting and using body tissue electrical signals.

The peripheral nerves in a human body, for example, produce and propagate electrical signals (sometimes called impulses) to do various jobs. Efferent nerves, for example, propagate signals from the central nervous system to muscles of the extremities to cause contraction or relaxation of the muscles. (For simplicity, we sometimes use the term "contraction" to refer to both contraction or relaxation.) Afferent nerves propagate signals in the other direction, from sensory organs including the skin to the central nervous system. One way to detect nerve electrical signals (impulse activity) is by the invasive technique of inserting an electrode through the skin and into the nerve; the nerve electrical signals can then be detected at the exposed end of the electrode.

Contraction or relaxation of muscles is caused by neurons at locations in the vicinity of, for example, muscles that operate the fingers. To activate a particular muscle (e.g., to cause it to contract), the brain can send a signal to a particular selected nerve having a bundle of neurons to cause the neurons to produce electrical signals. These electrical signals are based on the chemical process of interaction between neurons and between neurons and effector cells through the chemical messengers or neurotransmitters that are released. In the case of skeletal muscle cells, activated motor neurons transmit the neurotransmitter acetylcholine to the synapses of the skeletal muscle cells allowing the ion channels in that cell to open. This changes the membrane potential of the cell resulting in the sequence of events that causes an action potential and then a contraction of the muscle.

By sending coordinated electrical signals through selected nerves to corresponding muscles associated with a particular finger, for example, the brain can cause the finger to produce a wide variety of actions such as touching the palm. Thus, the brain can send signals through nerves to muscles in various parts of the body to cause parts of the body to move according to gestures intended by the brain, such as raising the index and middle finger of a hand in a "V". The gestures in turn can represent intent, for example, the intent to congratulate a teammate on a victory.

Other tissues of the body, such as brain cells, interneurons, and bones (which exhibit piezoelectric properties), also can produce electrical signals. Electrical signals produced by some tissues of the body are sometimes called action potentials.

SUMMARY

In general, in an aspect, bio-potentials (e.g., any electrical potential generated biologically that can be) are sensed on the skin of a subject. The bio-potentials include muscle bio-potentials and nerve bio-potentials. Skin sensors are positioned to enable the sensing circuitry to emphasize the nerve bio-potentials and deemphasize the muscle bio-potentials in processed bio-potential signals generated by the sensing circuitry. A machine learning component identifies control sequences or tracks body motions based on the processed bio-potential signals.

In general, in an aspect, electrical potentials are detected on the surface of the skin of a wrist or ankle (for example, or other body part), and the detected electrical potentials are processed to provide data values representing electrical signals occurring at nerves in the wrist or ankle.

Implementations may include any one or a combination of two or more of the following features. A structure supports the detectors and circuitry on the wrist. The detectors include electrodes. Alignment features align the structure relative to an upper surface and an outer edge of the wrist to position the detectors in contact with skin at the wrist or ankle and in the vicinity of particular internal tissues of the wrist. The alignment features are configured to position the detectors in contact with the top of the wrist or a particular surface of the ankle. The alignment features are configured to position the detectors in contact with the bottom of the wrist. The alignment features are arranged in a "J" and include a generally flat section to engage the upper surface of the wrist and a convex section to engage the outer side of the wrist. The alignment features are part of a single integrated rigid piece. The alignment features include flexible features. The alignment features include rigid features. The detectors are exposed at one or more internal surfaces. The detectors include pairs of detectors, one of the detectors of each pair being closer to the fingers or toes than the other detector of the pair. There can be at least two detectors, at least six detectors, at least twelve detectors, or at least one hundred detectors. At least one of the detectors is positioned to contact skin on the outer side of the wrist or ankle. At least one of the detectors is positioned to contact skin on the upper surface of the wrist. Each of the detectors includes a dry contact surface that is associated with a conductive solid, gel, foam, or film. Each of the detectors can be embedded in the alignment features as separate components, combined within a material used to form the alignment features, or can be fibers within a fabric. There is a resilient mounting for at least one of the detectors. The resilient mounting urges the detector to project from an inner surface. A band holds the structure on the wrist or ankle. The alignment features can interface with wearable tattoos or skin-based circuits. The alignment features include an edge to bear against a projection of the ulna (in the wrist example). The circuitry includes electronic components. The electronic components include a notch filter having an input coupled to at least one of the detectors. The electronic components include (e.g., a programmable hardware) bandpass filter associated with at least one of the detectors. The electronic components include an amplifier and an analog-to-digital converter. The electronic components include an inertial measurement unit. The electronic components include a wireless communication component. The electronic components include a processor to execute stored instructions to process digital signals derived from the detectors. The stored instructions are to cause the processor to produce data values. The stored instructions are to cause the processor to apply a process to extract features from data values and produce characterizations about gestures or intent or muscle contractions. The process includes a classifier. The stored instructions are to cause the processor also to use information from one or more other data sources. One of the other sources includes an inertial measurement unit. The stored instructions are to cause the processor to control a selection of groupings of two or more detectors from which signals will be acquired and processed as channels. One of the detectors in one of the groupings includes an electrode external to the wrist device. One of the channels is associated with three of the electrodes. The electronic components include a user interface. The user interface includes a display. The user interface includes one or more button controlled switches and a multi-color intensity controllable LED. The user interface includes haptic functions. There is a port for connection of an electrical conductor between the port and a detector configured to be adhered to the skin of the user. Functions are provided other than detecting electrical signals on the skin. The functional components include a time piece. A housing for the structure has the alignment features, a processor, a battery, a wireless communication module, and a user interface. There is a USB port for coupling a processor to an external digital device. There is a wireless communicator for coupling a processor to an external digital device.

In general, in an aspect, on the skin of a subject, electrical potentials are detected that are characteristic of electrical activity of neurological tissue and electrical potentials are also detected that are characteristic of electrical activity of non-neurological tissue in the vicinity of the detector. There is a processor, and digital storage containing instructions to be executed by the processor to cause the processor to produce data values representative of the electrical activity of the neurological tissue based on the detected electrical potentials.

Implementations may include any one or a combination of two or more of the following features. The instructions are to cause the processor to interpret the data values representative of the electrical activity of the neurological tissue as being associated with contractions of particular muscles. The instructions are to cause the processor to identify one or more gestures corresponding to the detected electrical potentials. The instructions are to cause the processor to identify intent corresponding to the detected electrical potentials. The instructions are to cause the processor to apply a process to features of the data to infer actions of particular muscles or gestures or intent based on known relationships of the features to the actions or gestures or intent. The process includes a machine learning process. The process includes a classifier process. The process includes a thresholding process. The electrical potentials are detected on the skin of the wrist of the subject. The detector includes electrodes to contact the skin of the subject. The detector includes electrodes to be used in pairs to detect differential electrical potentials on the skin. The detector includes a predefined pattern of electrodes to contact the skin of the subject, the instructions are to cause the processor to interpret the data as being associated with one or more gestures, muscle actions, or intent, and the system includes stored information representative of known relationships between electrical potentials detected by the predefined pattern of electrodes and corresponding gestures, muscle actions, or intent. There are one or more signal processing components to receive the detected electrical potentials and to produce processed electrical signals that are representative of, and have a better signal-to-noise ratio than, the detected electrical potentials of the neurological tissue. A spectral filter produces the processed electrical signals by spectral filtering the detected electrical potentials based on known spectral characteristics of electrical activity of neurological tissue. A notch filter produces the processed electrical signals by filtering out ambient electrical noise, based on known spectral characteristics, to obtain the biopotential signal. A temporal filter removes or attenuates frequencies in the biopotential signal. This helps to improve the signal-to-noise ratio of the signal. A spatial filter can determine each detector's amplitude based on the distance from each other. An analytical component produces the processed electrical signals by analyzing successive times of occurrence or changing polarity of electrical potentials at two locations on the skin and identifying electrical potentials characteristic of electrical activity of neurological tissue based on the relationship of the times of occurrence or the polarities. One or more electrical potentials characteristic of electrical activity of muscle tissue are detected on the skin of the subject, and the detected muscle tissue electrical potentials are used for noise cancellation with respect to the electrical potentials detected for the neurological tissue. An impedance matching component produces the processed electrical signals by matching the impedance of the detector to the impedance of the skin. The impedance is matched manually or dynamically. The impedance matching component controls a programmable resistor. The impedance matching component receives real-time measurements corresponding to the impedance on the skin of the subject.

The detector includes an array of electrical potential detectors and the instructions are to cause the processor to select a set of two or more of the detectors, the data being produced based on the electrical potentials of the selected set of detectors. There is a communication device. The instructions are to cause the processor to communicate the data to a therapy system through the communication device. The instructions are to cause the processor to communicate the data to a diagnostic system through the communication device. The instructions are to cause the processor to communicate the data to a control system through the communication device. The instructions are to cause the processor to communicate the data to a feedback system through the communication device. The instructions are to cause the processor to communicate the data to a research system through the communication device. The instructions are to cause the processor to communicate the data to a performance measurement system through the communication device. The instructions are to cause the processor to perform a calibration operation. The instructions are to cause the processor to communicate the data to an augmented reality or virtual reality system through the communication device.

In general, in an aspect, a device is controlled using electromyography signals measured from a skin surface using one or more surface electromyography sensors and a sensor hub.

In general, in an aspect, gesture or intent information is determined based on nerve electrical activity and is provided to an application.

Implementations may include any one or a combination of two or more of the following features. The instructions to be executed by the processor are to cause the processor to receive the gesture or intent information wirelessly from a device having electrical potential detectors on the skin of a user. The instructions to be executed by the processor are to cause the processor to receive other information not representing electrical potentials detected on the skin of a user, and to generate the gesture or intent information based also on the other information. The other information includes inertial information from an inertial measurement unit. The processor is part of the user device and the instructions to be executed by the processor are to cause the processor to provide the gesture or intent information to two or more other applications running on the user device. The gesture or intent information is received wirelessly from two or more such devices and is expressed in a device-independent format. The gesture or intent information is associated with a succession of times based on nerve electrical activity occurring at the succession of times. The gesture or intent is based on motion of one or more fingers and the gesture or intent information is provided to the application for use with a physics model of finger motion to control motion of fingers on a user interface. The instructions to be executed by the processor are to cause haptic feedback to a subject who is the source of the gesture or intent.

In general, in an aspect, on the skin of a subject, electrical potentials are detected that are characteristic of electrical activity of tissues including electrical potentials characteristic of each of nerve tissue and muscle tissue. The instructions to be executed by the processor are to cause the processor to produce data representative of the separate electrical activity of each of the tissues based on the detected electrical potentials.

Implementations may include any one or a combination of two or more of the following features. The instructions are to cause the processor to interpret the data representative of the electrical activity of the respective tissues as being associated with actions of particular muscles. The instructions are to cause the processor to infer one or more gestures or intent corresponding to the detected electrical potentials for respective tissues. The instructions are to cause the processor to apply a process to features of the data to infer actions of particular muscles or gestures or intent based on known relationships of the features to the actions, intent, or gestures. The process includes a machine learning process. The process includes a classifier process. The electrical potentials are detected on the skin of the subject. The electrical potentials are detected on the skin of the wrist. The sensor includes electrodes to contact the skin of the subject. The sensor includes electrodes to be used in pairs to detect differential electrical potentials on the skin. The sensor includes a predefined pattern of electrodes to contact the skin of the subject, the instructions are to cause the processor to interpret the data as being associated with one or more gestures, and the system includes stored information representative of known relationships between electrical potentials detected by the predefined pattern of electrodes and corresponding gestures. One or more signal processing components receive the detected electrical potentials and produce processed electrical signals that are representative of, and have a better signal-to-noise ratio than, the detected electrical potentials. The producing of the processed electrical signals includes spectral filtering the detected electrical potentials based on known spectral characteristics of electrical activity of respective tissues. The producing of the processed electrical signals includes notch filtering the detected electrical potentials based on known spectral characteristics of ambient noise. The producing of the processed electrical signals includes matching the impedance of the sensor to the impedance of the skin. The impedance is matched dynamically. The impedance matching includes controlling a programmable resistor. The impedance matching includes receiving real-time measurements corresponding to the impedance on the skin of the subject. The sensor includes an array of electrical potential detectors and the instructions are to cause the processor to select a set of two or more of the detectors, the data being produced based on the electrical potentials of the selected set of detectors. The instructions are to cause the processor to select a series of sets of detectors, the data being produced based on the electrical potentials form each of the sets of detectors. There is a communication device. The instructions are to cause the processor to communicate the data to a therapy system, a diagnostic system, a control system, a feedback system, a research system, or a performance measurement system. The instructions are to cause the processor to interpret the data representative of the electrical activity of the neurological tissue as being associated with intentions of the subject. The instructions are to cause the processor to perform a calibration operation. The instructions are to cause the processor to communicate the data to an augmented reality or virtual reality system.

In general, in an aspect, activation of movement of an appendage of a vertebrate subject is monitored. A set of at least two electrodes contacts a skin surface of the vertebrate in a location proximate to a neuromuscular bundle associated with the appendage. A matrix mounts the set of electrodes in position in the location. A signal processing unit has an input coupled to the electrodes and an output. The unit includes: an amplifier system coupled to the unit's input and having an output; a filter system that passes neuronal signals and attenuates other signals; and a postprocessor coupled to the output.

Implementations may include any one or a combination of two or more of the following features. The postprocessor is a metering device to provide a measure of a level of neuronal activity associated with the activation of movement. The postprocessor includes a threshold processor to provide an output only when a level of neuronal activity exceeds a threshold.

In general, in an aspect, and apparatus includes a processor and a digital storage containing instructions executable by the processor to (a) determine gesture or intent information of a person based on nerve electrical activity detected on skin of the person and (b) provide the gesture or intent information to an application, the gesture or intent being about motion of the hand or wrist or finger or a combination of them of the person.

Implementations may include one or a combination of two or more of the following features. The motion includes rolling, tilting, or yawing of the hand or the wrist or a combination of the hand in the wrist. The motion includes rotating or twisting the hand and wrist. The gesture or intent information includes at least one of direction, orientation, rate of motion, or magnitude. The motion corresponds to manipulation of a sphere. The gesture or intent information is associated with a motion of a displayed element of a displayed user interface of the application. The displayed element includes a sphere or an element analogous to a sphere. The displayed element is proportional to the motion of the gesture or intent. The motion of the displayed element is not necessarily proportional to the motion of the gesture or intent. The motion of the displayed element is translated to motion of the displayed element according to a mapping. The magnitude of the motion of the displayed element is a multiple of the magnitude of the motion of the gesture or intent. The magnitude of the motion of the displayed element is based on a magnitude of acceleration of the motion of the gesture or intent.

Other aspects, implementations, features, and advantages, and combinations of them, can be expressed as methods, apparatus, systems, components, means and steps for performing the function, program products, software, business methods, and in other ways.

Other aspects, features, implementations, and advantages will become apparent from the following description, and from the claims.

DESCRIPTION

Figure 3A:
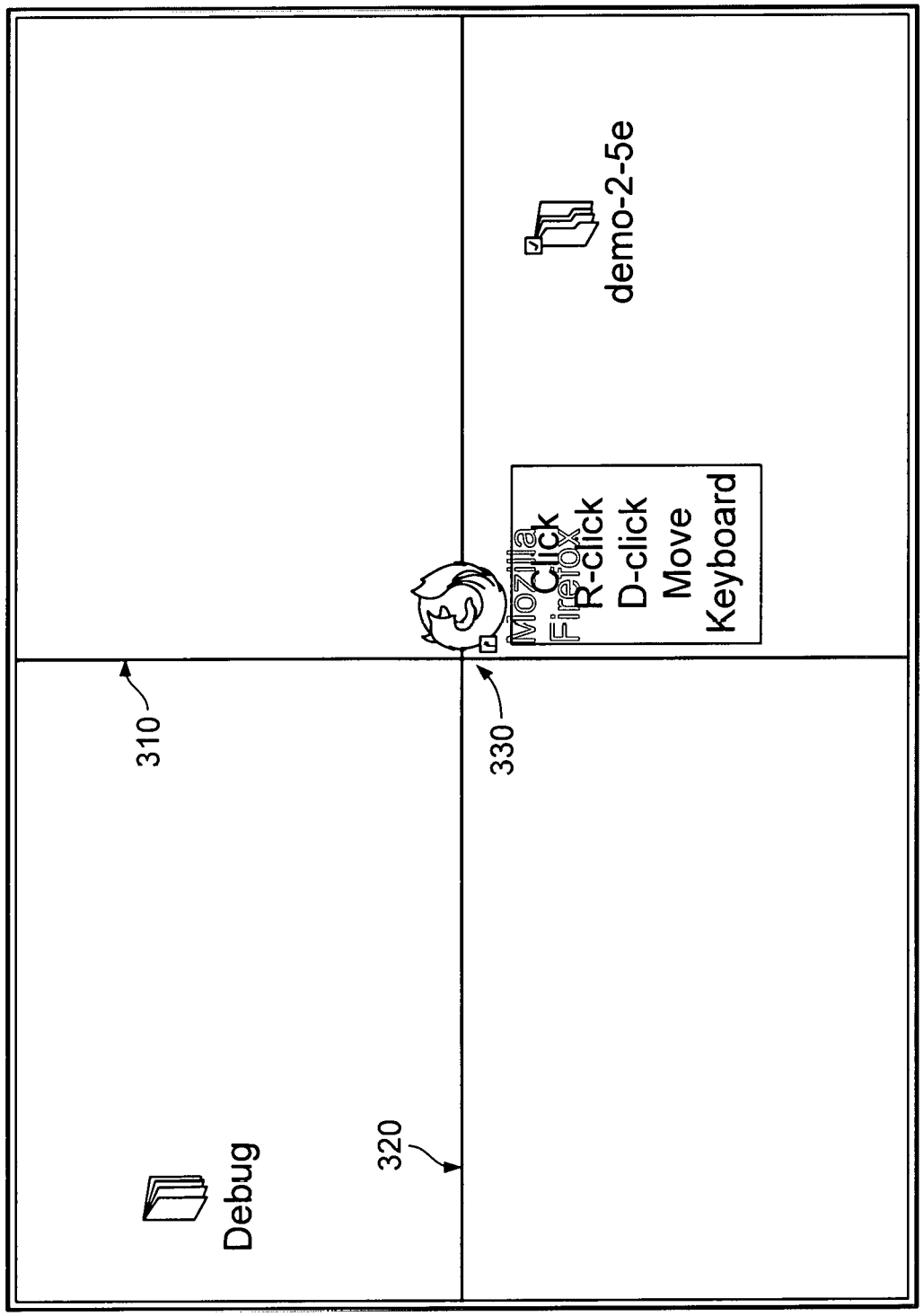
Figure 3B:
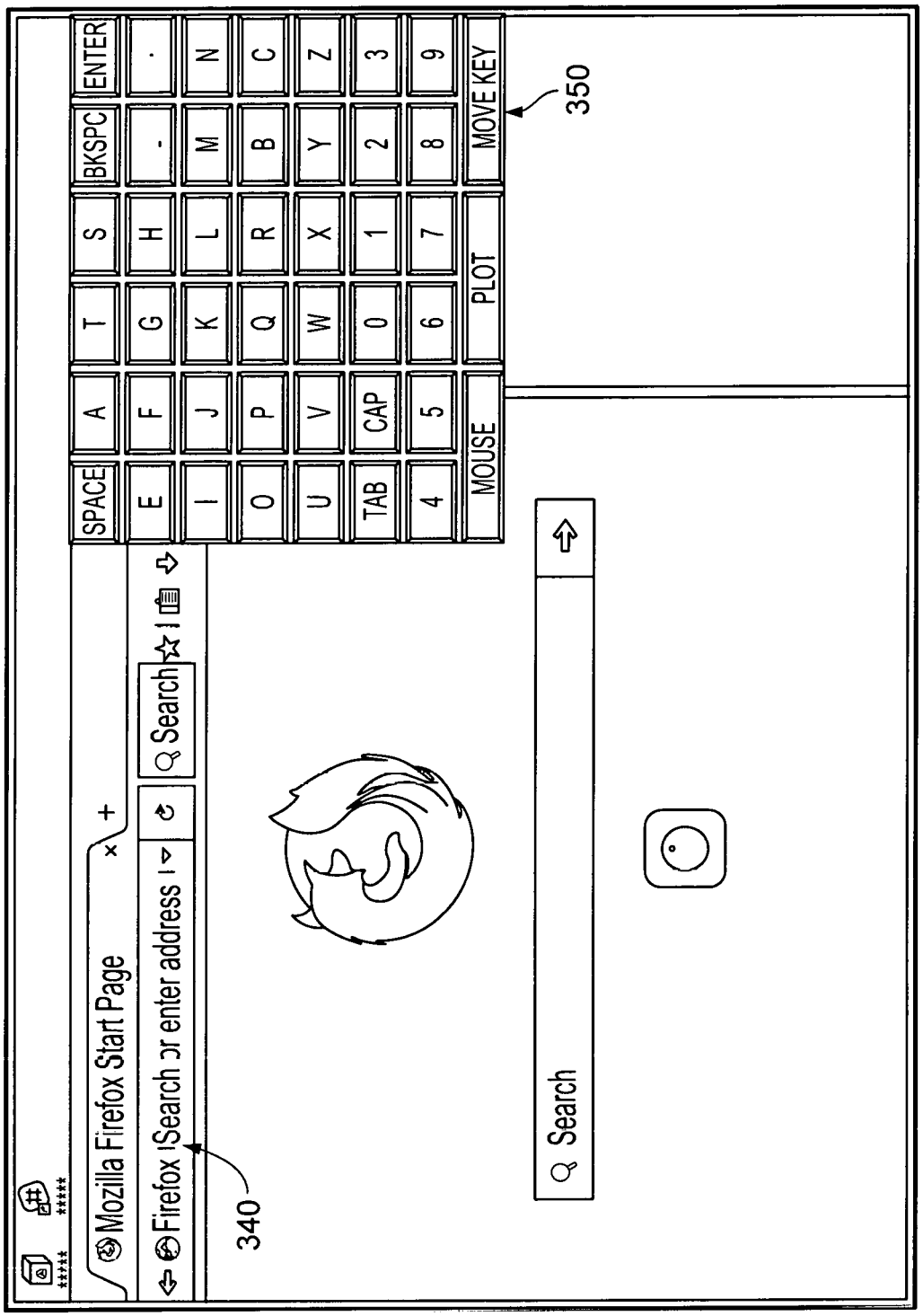
Figure 3C:
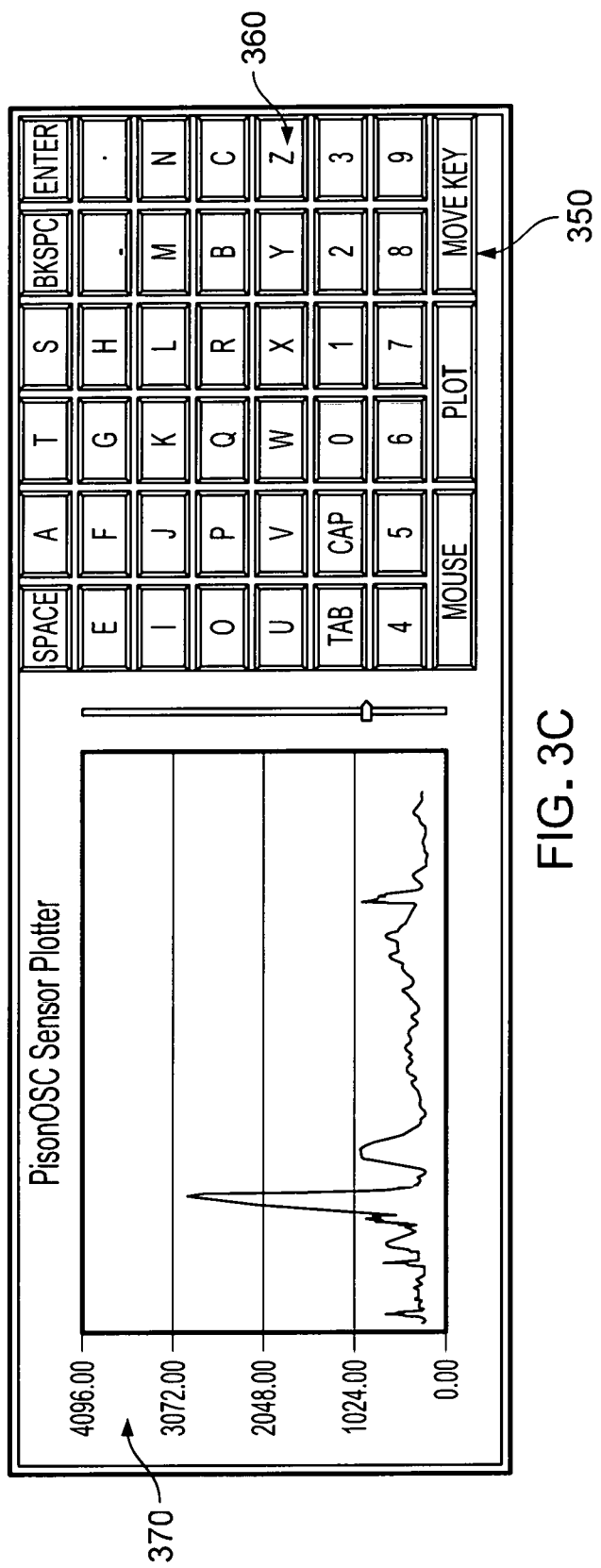
Figure 4:
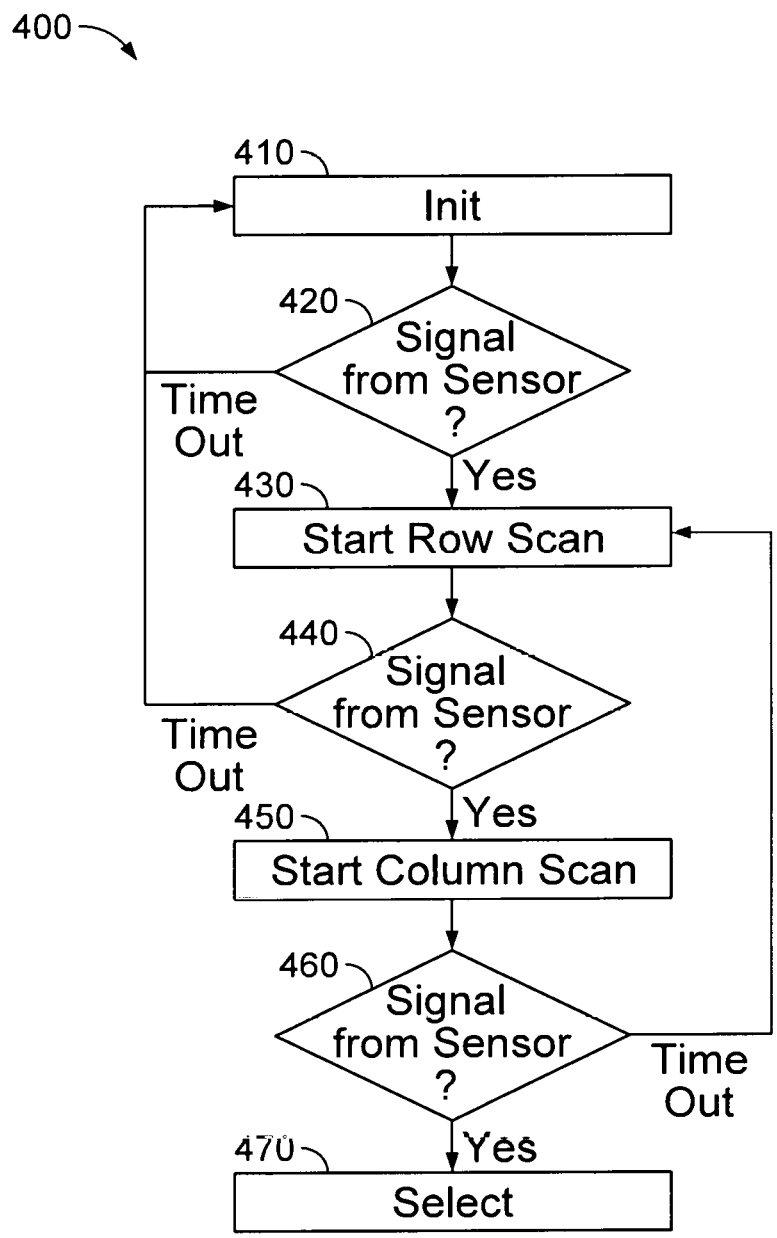
Figure 5:
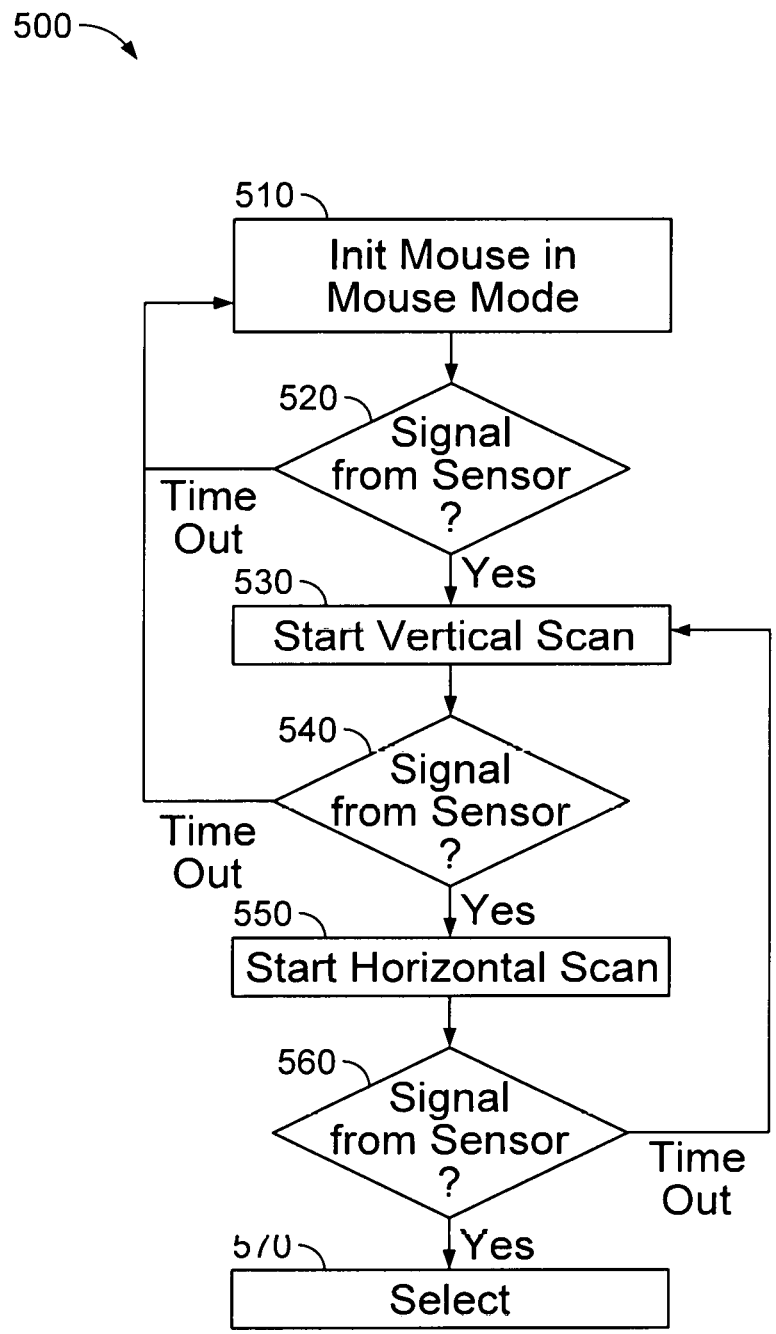
Figure 6:
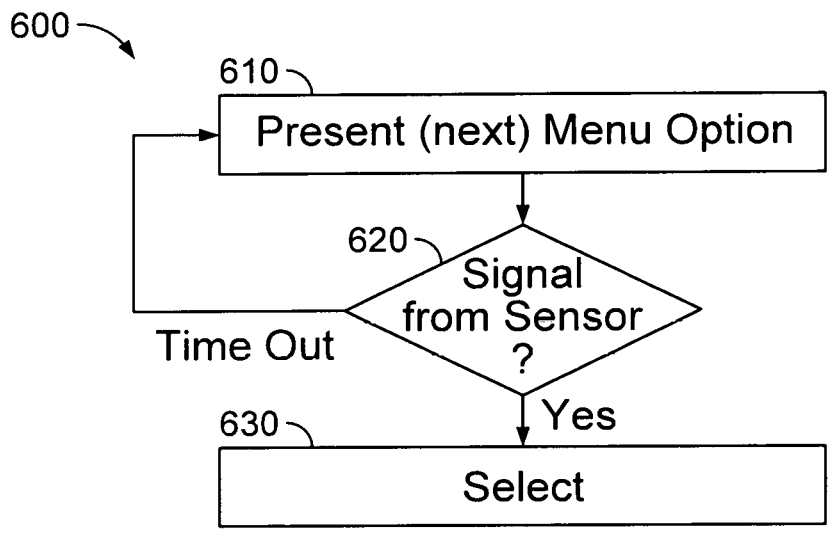
Figure 7:
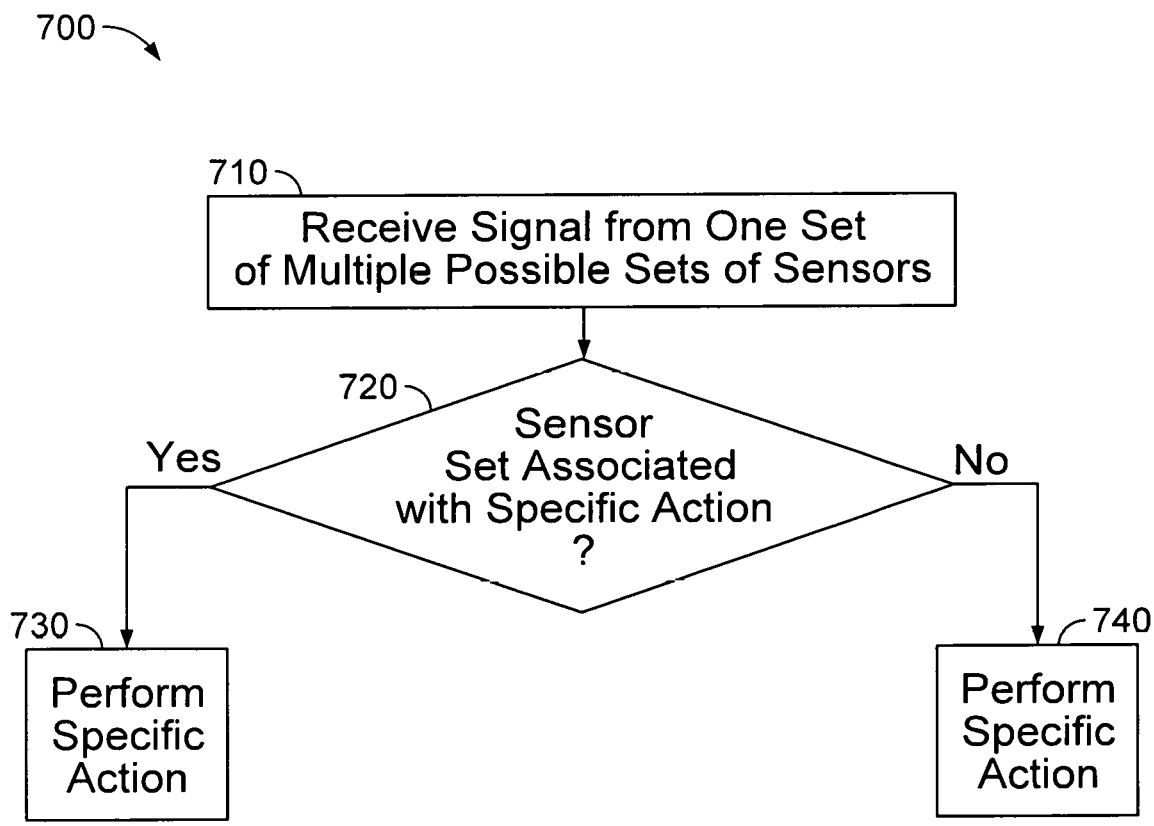
Figure 8:
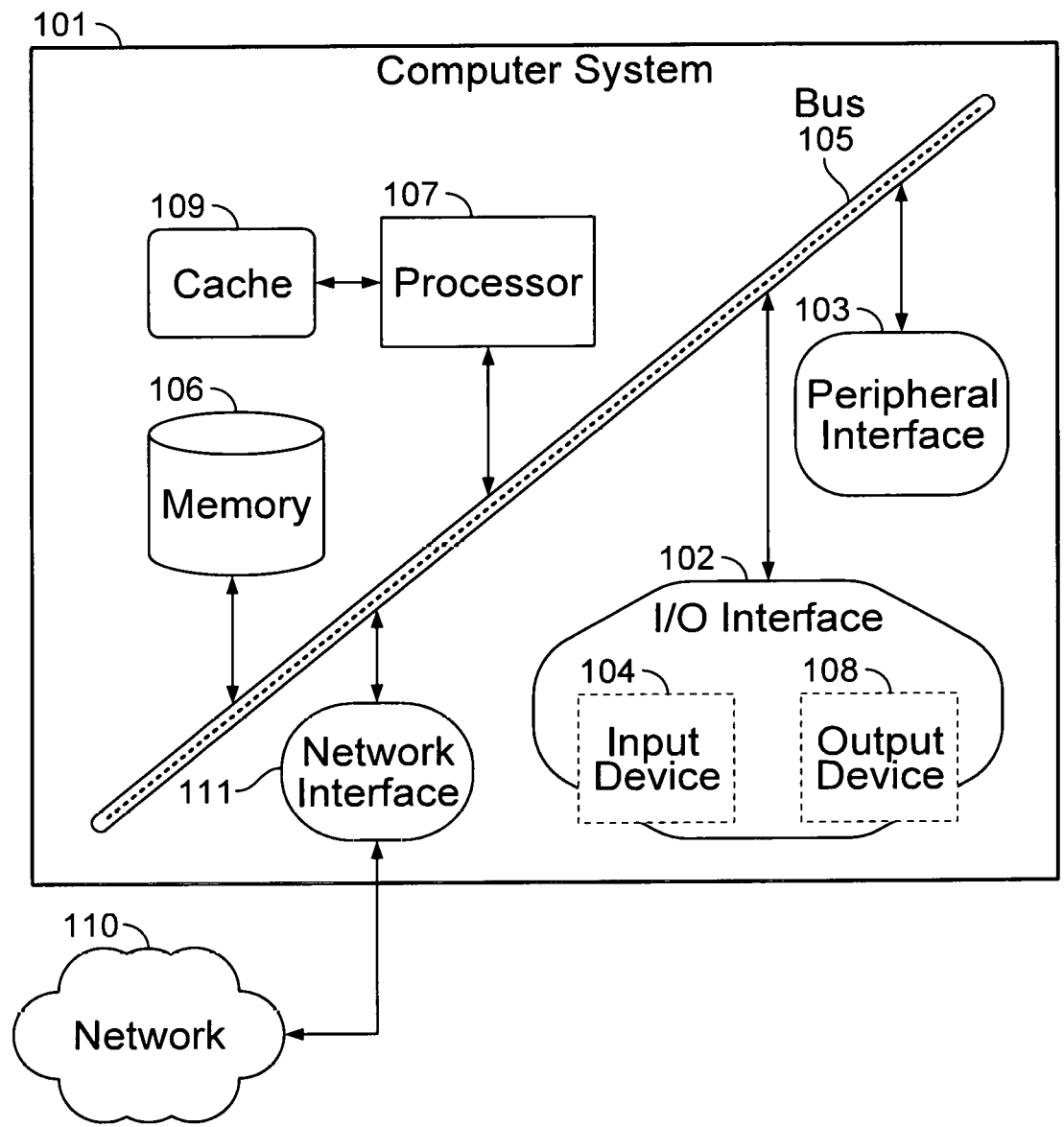

FIG. 3A, FIG. 3B, and FIG. 3C are screen images for an example implementation of a sensor monitor and interface;

FIG. 4 is a flowchart for an example method of selecting a matrix field using sEMG sensors;

FIG. 5 is a flowchart for an example method of operating a pointer using sEMG sensors;

FIG. 6 is a flowchart for an example method of selecting a menu option using sEMG sensors;

FIG. 7 is a flowchart for an example method of differentiating multiple sEMG sensors; and FIG. 8 is a block diagram of a computing system suitable for use in the various implementations described.

Figure 9:
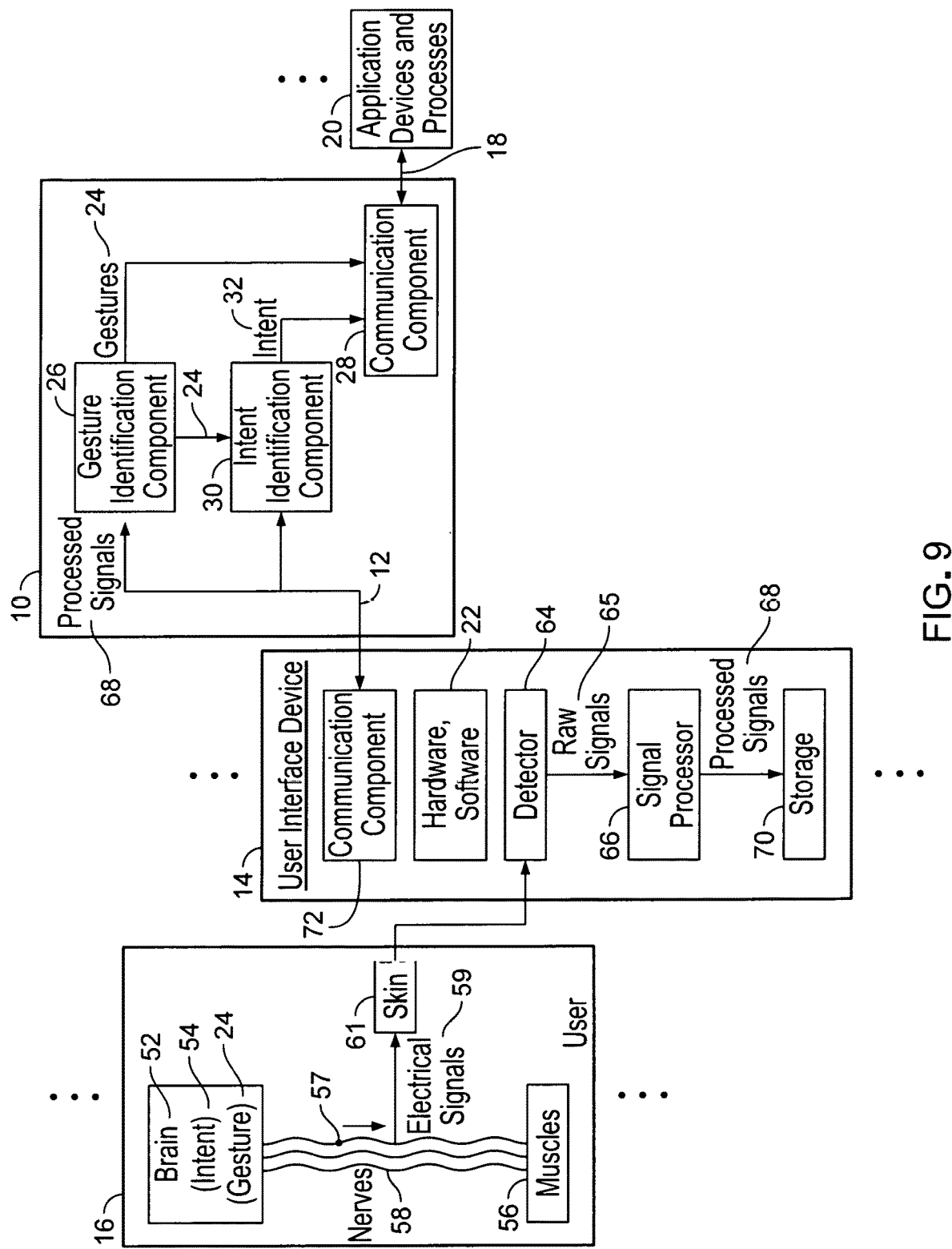

FIG. 9 is a schematic block diagram.

Figure 10:
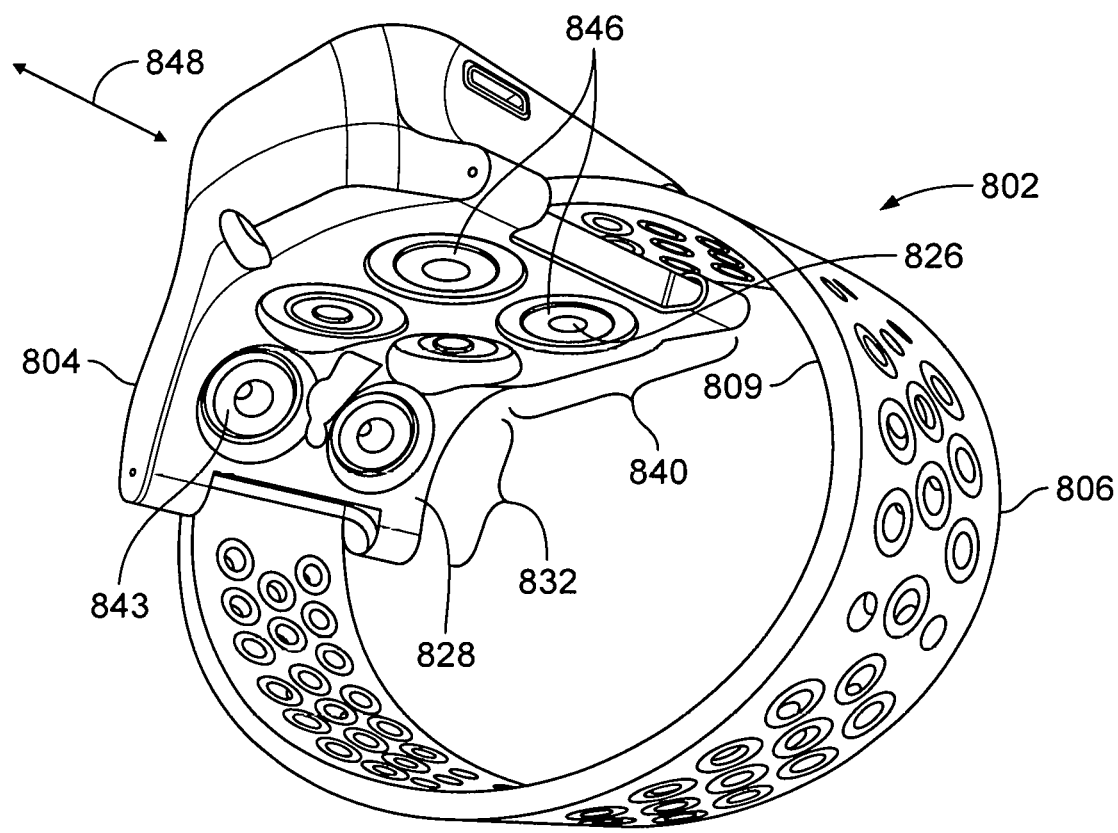

FIG. 10 is a perspective drawing of a wrist device.

Figure 11:
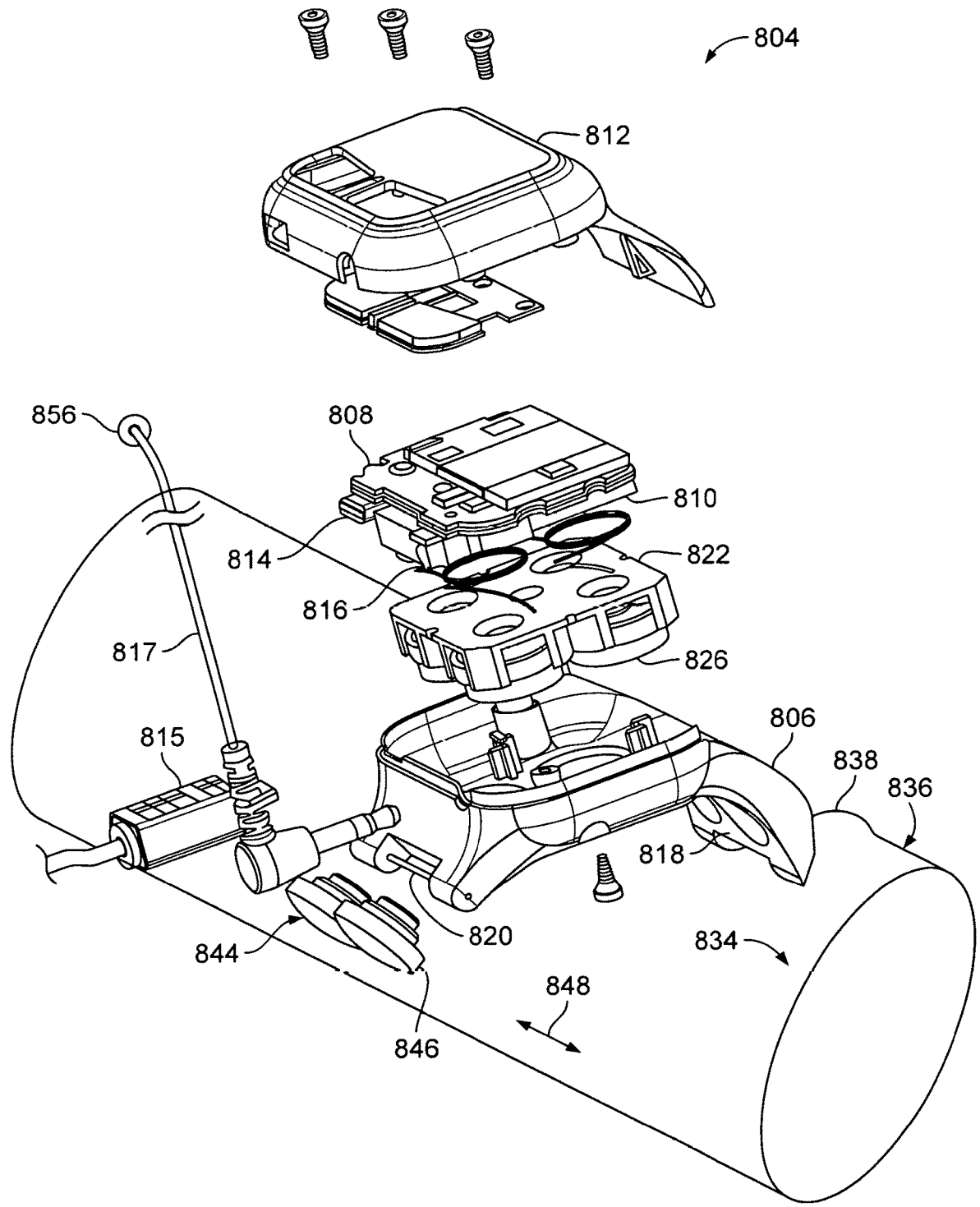

FIG. 11 is an exploded perspective drawing of a wrist device.

Figure 12:
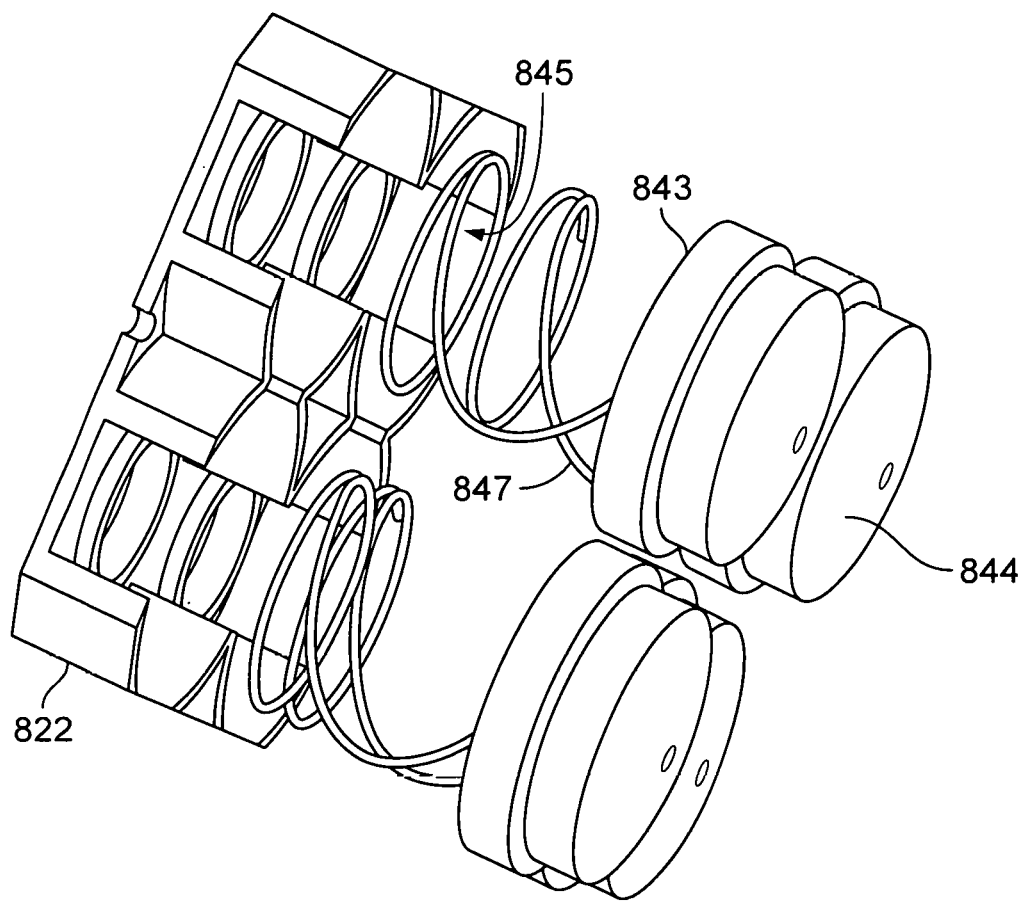
Figure 13:
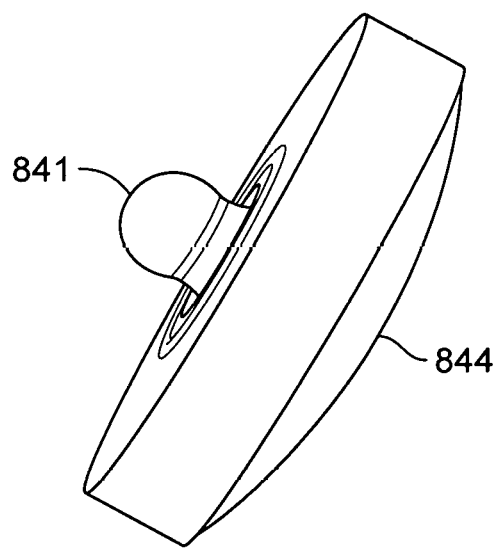
Figure 14:
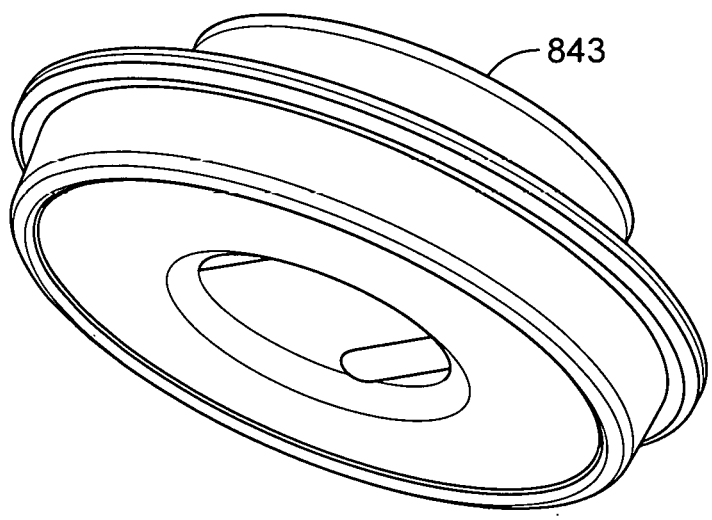

FIGS. 12, 13, and 14 are perspective, side, and perspective views respectively of an electrode snap arrangement.

Figure 15:
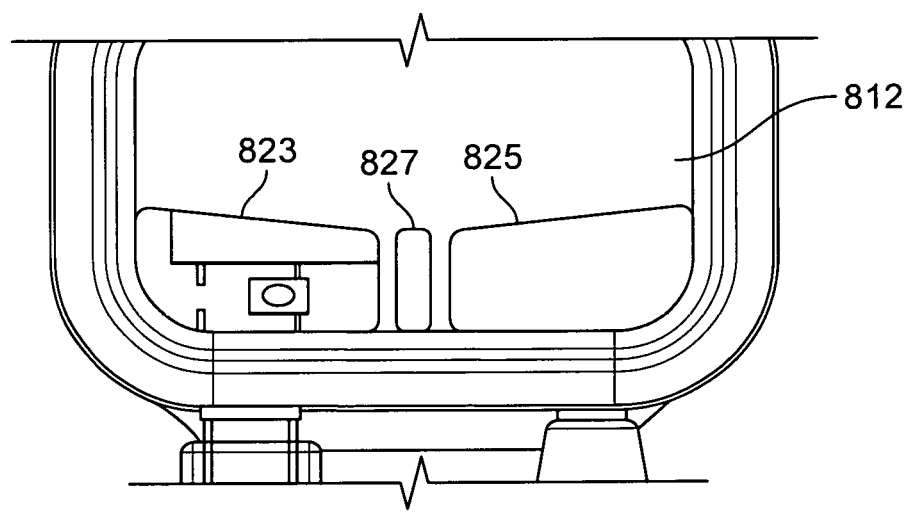

FIG. 15 is a top view of part of a wrist device.

Figure 16:
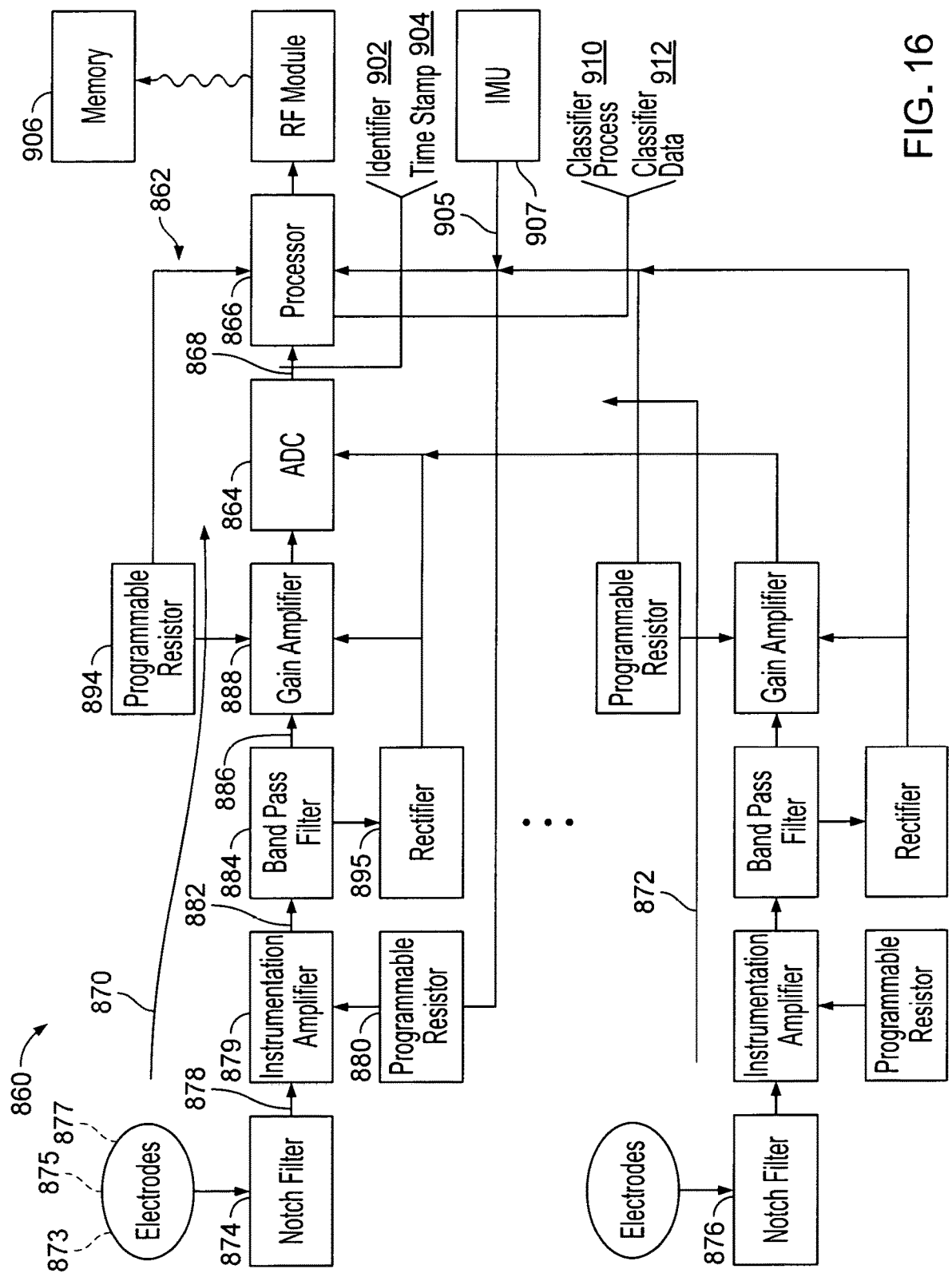

FIG. 16 is a block diagram of signal processing circuitry.

Figure 17:
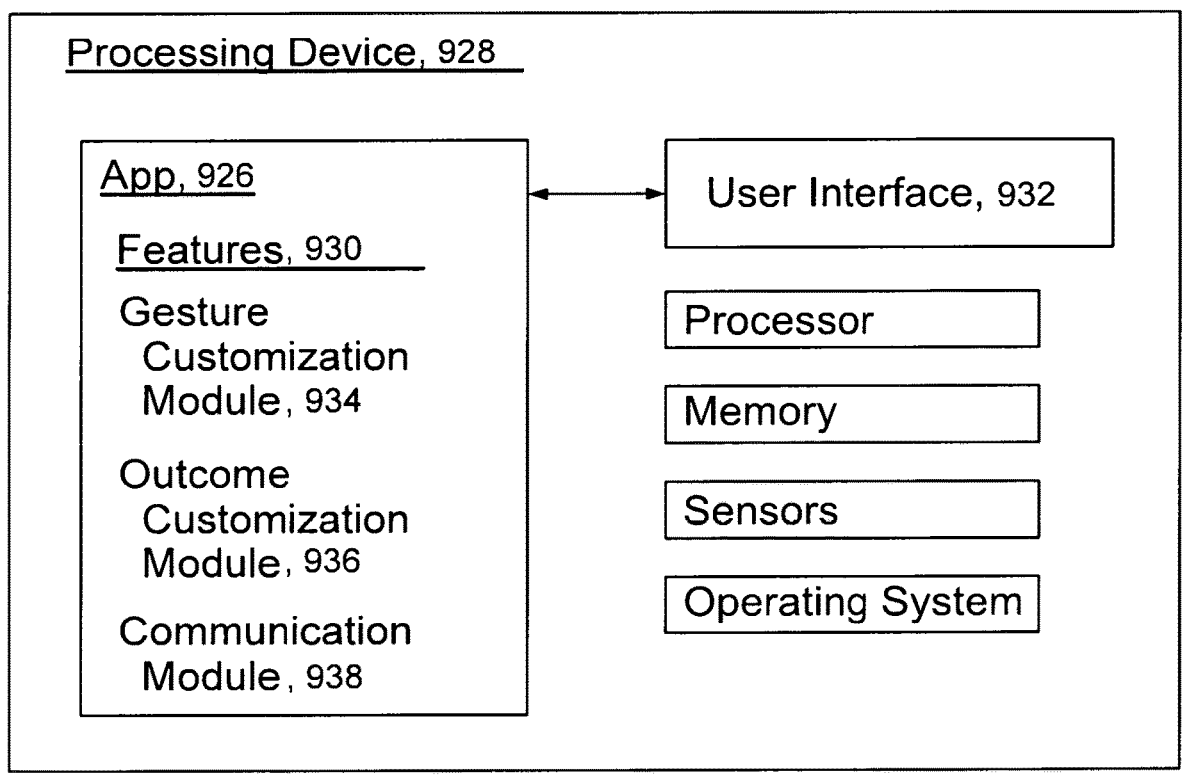

FIG. 17 is a block diagram of a processing device.

Figure 18:
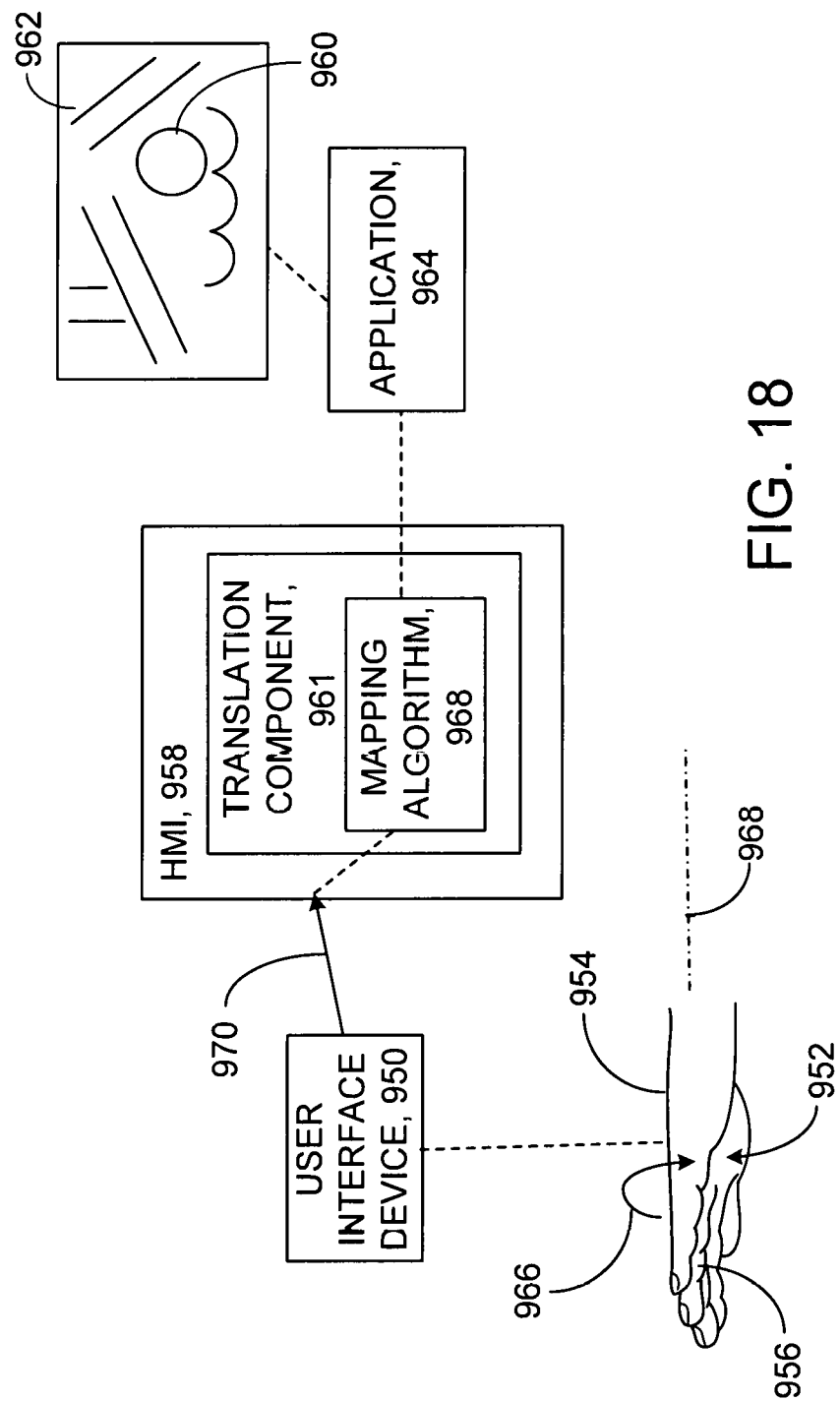

FIG. 18 is a schematic diagram of control of a displayed user interface.

Figure 19:
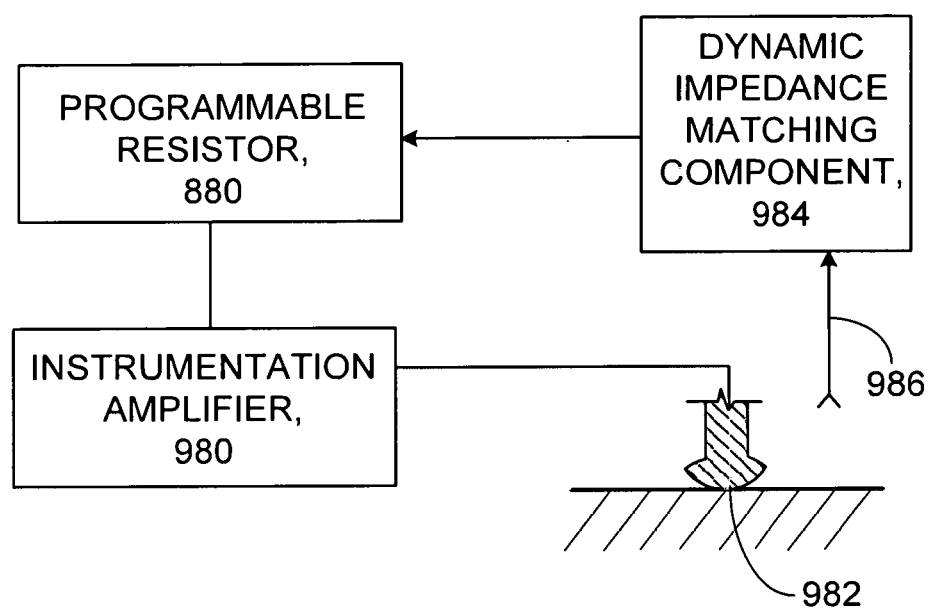

FIG. 19 is a schematic block diagram.

OVERVIEW

Here we describe, among other things, technologies that can detect tissue electrical signals (in particular, nerve electrical signals) non-invasively, accurately, and precisely, and use information about the electrical signals for a wide variety of purposes including diagnosis, therapy, control, inference of gestures or other indications of intent, biofeedback, interaction, analysis, and study, to name a few. Because the information about the electrical signals can be more accurate and precise than other techniques, the purposes for which they are used can be more effective, faster, simpler, subtler, and more productive, among other things. New applications not currently possible can also be implemented.

We use the term "nerve" broadly to include, for example, any part of a body that carries signals, particularly electrical signals (e.g., electrochemical signals) between parts of the body. Nerves include efferent nerves that are part of the peripheral nervous system and cause muscles to, for example, contract or relax, and we sometimes use the term "nerve" to refer to efferent nerves. Nerves also include afferent nerves that carry signals as part of the sensory nervous system, and we sometimes use the term "nerve" to refer also to afferent nerves. A nerve typically comprises a bundle of fascicles each of which comprises a bundle of neurons.

We use the term "electrical signal" broadly to include, for example, any event, occurrence, or phenomenon that can be detected electrically, such as electrical potential, resistance, capacitance, inductance, other impedance, or current. We sometimes use the term "electrical signal" to refer to such an event, occurrence, or phenomenon that occurs at a place in the body, can propagate through tissues of the body, and may be detected or sensed at a (e.g., nearby) location on the skin. For simplicity, we sometimes use the term "electrical potential" broadly to include, for example, electrical potential, resistance, capacitance, inductance, other impedance, or current.

As an electrical signal propagates along a given nerve, it can be detected at a succession of locations along the length of the nerve and its direction and speed of propagation can be determined by detecting the times of appearance and the polarities of the electrical signal at two (e.g., closely) spaced apart locations and determining how much time has elapsed between those times.

In our discussion, we often use as an example the detection and use of nerve electrical signals that appear in the wrist. The technologies that we describe here also can be useful for detecting and using nerve electrical signals or other tissue electrical signals at any other part of the body, especially the extremities.

Although the technologies that we describe here apply to any part of the peripheral nervous system generally, they are particularly useful for the somatic or voluntary nervous system which effects voluntary control of skeletal muscles.

In the physiology of the human body, specific nerves or parts of them may be embedded in or closely associated with muscles, bones, and other tissues. Electrical signals in the body may occur not only in nerves, but also in muscles, bones, and other tissues (all of which we sometimes refer to as "signal sources").

Many parts of the human body contain combinations of these signal sources intertwined, overlaid, or otherwise near to one another. An electrical signal occurring at one of the signal sources typically propagates in all directions and is attenuated and dispersed to degrees determined by the distances it propagates and by the attenuation properties of other tissues through which it propagates. Eventually the propagated, attenuated versions of the original electrical signals that occurred at the signal sources reach the surface of the skin where they form detectable electrical potentials, for example. Because electrical signals from two or more of the signal sources (say a muscle and a nearby nerve) can occur at roughly the same time, the electrical potential at a given location on the skin at a given time typically represents a complex aggregation of electrical potentials that result from electrical signals occurring at multiple signal sources. The electrical potentials that appear at a given time and at successive times at an array of locations in a given region on the surface of the skin, say at the wrist, therefore are indicative of specific electrical signals occurring at each of the signal sources in the vicinity of that region within the body at that given time and sequence of times.

By detecting electrical potentials at such an array of locations in the given region on the skin and processing information representing those electrical potentials, the technologies that we describe here can be used to identify, map (two-dimensionally or three-dimensionally), observe, store, and use (for a wide variety of purposes) accurate and precise information about the electrical signals occurring at specific identifiable signal sources (for example, specific efferent nerves associated with the contraction of the thumb and the extension of the four fingers) at a given time or over a sequence of times. The information about the electrical signals can be associated with specific individual muscles, tendons, and nerves. The relative sizes of electrical potentials detected at different locations can be used to infer which muscle or nerve is the source of an action potential. As explained later, when the electrical potentials are detected at multiple locations on the skin, machine learning is one way to determine the specific muscle or nerve that is electrically active. As also discussed later, in some cases the determination can be made based simply on thresholds of amplitude. The relative amplitudes of the detected differential signals at different locations can be used to infer which muscle or nerve is electrically active.

In examples in which electrical signals are determined to have occurred at specific nerves, the technology can effectively determine which muscle is the target of intended motion or is about to move without the need to detect the electrical signals directly associated with contraction of the muscles.

In some implementations, detected electrical potentials are not associated with particular nerves controlling particular target muscles. In these other implementations, the nerve electrical signals are detected at certain locations and are matched with known physiology to map the detected electrical signals to corresponding target muscles. Electrodes help us map to particular muscles based on physiology. In experiments with people with ALS, who have atrophied non-moving muscles, the technology can detect nerve electrical signals and determine that they correspond to intended gross muscle movement even though there is no physical movement or muscle electrical signal present.

Therefore, of particular interest among the signal sources in, say, the wrist, and in the information that can be generated from the detected electrical potentials, are details about when and to what degree electrical signals occur at the specific efferent nerves that control the muscles of the hand at a given time or a sequence of times. The muscles of the hand have an important role in how the human body interacts (for example through the fingers) with the external world. The information that can be generated by the technologies that we describe here can enable a wide range of devices, systems, processes, and other applications that rely on understanding when, how, and the extent to which the muscles of the hand have been or are going to be contracted or relaxed and on gestures and intent represented by those contractions or relaxations.

The muscles of the body produce electrical signals when they contract or relax. Those muscle electrical signals can be detected by surface electrodes on the skin of the body in the vicinity of the muscle using surface electromyography ("sEMG") and can be used for various purposes. A pair of skin electrodes (located at the upper forearm, for example) is typically used to detect a voltage differential as an indicator of the electrical activity in the muscle. The detected voltage differential can be used to determine that the brain intended to cause (or is about to cause or has actually caused) the corresponding muscle to, for example, contract. The contraction could be, for example, of a muscle of the index finger that would have the effect of clicking a computer mouse button if the hand were holding a mouse. And, even if the hand were not holding a mouse, a processor could translate the voltage differential signals from the muscles into the intended action (clicking the mouse) by causing a program to do what would have been done had a real mouse button actually been clicked.

Although some existing systems can enable some such applications by detecting electrical signals that occur in the contraction or relaxation of the muscles themselves, there are advantages in being able to detect directly and process information about the electrical signals in the nerves such as the efferent nerves that trigger the electrical signals in the muscles. The electrical signals that occur at the efferent nerves are more direct, precise, earlier-appearing indicators of activity at the brain than are the corresponding electrical signals generated by contraction of the muscles.

Many applications are designed to cause actions (for instance, the selection of a menu item on a user interface) based on information that is representative of intent of a user expressed by the signals propagated by the brain to the efferent nerves. Existing electrical potential detection systems use muscle contraction electrical signals as a proxy for inferring the intention signals propagated by the brain. Among other things, the nerve electrical signals detected and processed by the technologies described here are received slightly sooner than the resulting muscle contraction electrical signals, can be more precise as indicators of intention than the muscle contraction signals, and can avoid errors that can happen when a muscle contraction does not in fact accurately represent the intention carried in the nerve electrical signal. The latter can happen for a variety of reasons, such as, when the muscles are not working or not working properly or have atrophied or are missing (for example, patients affected by ALS, stroke, or amputation).

The technologies that we describe here provide more accurate and precise measurements of nerve electrical signals and electrical signals of other tissues than any known system. As a result, more effective and new applications for information about tissue electrical signals are made possible. Among other things, characterizations of gestures or intent associated with the tissue electrical signals can be more accurate due to less cross talk among electrical signals generated by different tissues, for example, when muscle contractions (and the associated muscle electrical signals) could be appearing in multiple muscles at the same time.

As mentioned above, nerve electrical signals can be more accurate and fine-grained indicators of muscle contraction and relaxation than muscle electrical signals. Yet nerve electrical signals are often of smaller magnitude than muscle contraction signals. And all electrical potentials detected on the surface of the skin are subject to "noise", including 60 Hz noise from nearby electrical devices, electrical signals from muscle, bones, and other tissues, variation in the electrical properties of the skin, and other sources of noise.

The technologies that we describe here use various strategies and combinations of them to improve the signal-to-noise ratio for the electrical potentials detected on the skin. In implementations, these strategies can include one or more of the following:

1. Electrical signals occurring in different types of tissue and occurring in the body for different purposes may have different spectral characteristics. For example, the typical frequency range of muscle contraction electrical signals is 20 Hz to 300 Hz with dominant energy in the 50 Hz to 150 Hz range while the typical frequency range of nerve electrical signals is 200 Hz to 1000 Hz. By applying appropriate filters during signal processing of the detected electrical potentials, it is possible to enhance, for example, the relative strength of the nerve electrical signals.

2. Some parts of the body (such as the wrist) contain relatively little muscle tissue and, in particular, relatively little of the bulky part of muscle tissue that produces the predominant portion of the force resulting from contraction of the muscle. Placement of the electrical potential detectors on the skin at parts of the body that have relatively little such muscle tissue can reduce the relative amplitude of "noise" that the muscle contraction electrical signals produce at the skin surface.

3. In some parts of the body (such as the wrist), the nerves for which the nerve electrical signals are to be detected lie between the detector on the surface of the skin and muscle or other tissue. Therefore, electrical signals occurring at the other tissues may be blocked or attenuated by intervening tissue on their way to the skin. As a result, placement of the electrical potential detectors on the skin at such a body part can reduce the "noise" in the electrical potential signals associated with the nerve.

4. The way the electrical signals from multiple signal sources combine at the surface of the skin can be sensitive to the specific location or pattern of locations on the skin at which electrical potential detectors are placed. There is a scientific basis for detector placement based on the physiology and arrangement of nerves. In one location, the portion of the measured electrical potential attributable to nerve electrical signals can have a lower signal-to-noise ratio than at a nearby location that is within a centimeter or less of the first location. Therefore, adjusting the locations of the detectors in small increments to locate the highest signal-to-noise ratio locations can be useful.

5. In applications of the technologies that we describe here, movements of parts of the body caused by contractions or relaxations of muscles are inferred from electrical potentials (and patterns of them) measured at a given time or at a sequence of times at two or more locations on the skin. Information about the inferred movements of parts of the body can then be provided to applications for a wide variety of purposes. Many different approaches can be used for making such inferences. Basic machine learning algorithms like Fine Gaussian support vector machines (SVMs) when trained on a representative feature set are able to achieve high accuracy while maintaining low computational complexity. As more user data is aggregated, the accuracy of the model will increase if the feature set is representative of the actions being distinguished from one another. If the extracted feature set is not representative or does not increase in accuracy more computationally intensive learning frameworks can be used to identify features. Deep neural nets have been shown to be effective in identifying a concise and representative feature set. However, this feature set may not rely on the underlying biology and may reduce the ability to make inferences about the system. Among such approaches are those in which known relationships between the electrical potentials at the skin surface and corresponding actual movements of parts of the body are used to train machine learning processes to recognize relationships between features extracted from the electrical potentials and the corresponding movements of parts of the body. Such known relationships can be obtained from people in various ways. The choice of which known relationships are used for training and the choice of machine learning process to which they are applied may affect the speed and accuracy of the inferences. In some implementations, useful relationships for training can be derived from people whose relevant muscles have atrophied or do not function for some other reason. In such cases, because muscle contraction electrical signals do not occur, it is possible to reduce the impact that would otherwise be caused by such relatively large magnitude unwanted electrical signals. In general, the nerve electrical signals that correspond to putative muscle contraction in such people are the same as the nerve electrical signals that correspond to actual muscle contraction in people whose muscles function properly. Historical training can take advantage of this same principle.

6. Because muscle contraction electrical signals may represent a significant source of "noise" and electrical potentials associated with those electrical signals may be available at the surface of the skin, it is possible to disambiguate muscle electrical signals from aggregate detected electrical potentials. The noise can be reduced by detecting the electrical potentials at locations that are nearer to the muscles than the locations where the nerve electrical signals are being detected. Then, the muscle electrical signals can be canceled from the nerve electrical signals.

7. Electrical signals from the brain (impulses, action potentials) propagate along nerves at speeds that are characteristically different from the localized occurrence of electrical signals in muscle (which contract "in place"). Nerve electrical signals directed at target muscle contraction placement can travel as fast as 119 m/sec. Pain electrical signals can travel more slowly, for example, at 0.61 m/sec, and touch electrical signals can travel at, for example, 76.2 m/sec. By placing electrical potential detectors (e.g. skin surface electrodes) of a given pair in positions and relative orientations such that the electrical potential change caused by a propagating impulse will appear first at one of the detectors and at a measurable time later at the other of the detectors, it is possible to determine the direction of propagation and the speed of propagation of the impulse. This information enables the technologies that we describe here to distinguish between muscle electrical signals and nerve electrical signals. Similar approaches may be useful to distinguish electrical signals of bones or other tissues.

8. Nerves include bundles of neurons some of which have motor functions (to cause muscles to contract or relax) and some of which have sensory functions (to report sensed stimuli back to the brain). In detecting nerve electrical signals, it is useful to distinguish between motor and sensory nerve electrical signals. By detecting the polarity of a differential signal between two electrodes placed nearer to and farther from the fingers, it is possible to identify the direction of propagation and therefore to disregard sensory nerve electrical signals based on the polarity.

In order to reduce noise and improve the signal-to-noise ratio various techniques or components can be utilized. One such technique is to add conductive or magnetic material around the electronic components to act as a shield from electromagnetic interference. Capacitors can be added into the circuit to act as reservoirs to smooth voltage variations. Chokes, or inductances, can be added to the circuit to smooth current variations. Low pass filters, high pass filters, band pass filters, and band stop filters can all be created physically or digitally to attenuate noise in a signal. High pass filters only allow high frequency signals to pass through them. Low pass filters only allow low frequencies to pass through them. Band pass filters only allow a certain range from one frequency to another to pass through them. Band stop filters attenuate frequencies in a range of one frequency to another and allow all others to pass through. The frequencies that these filters allow or attenuate can be adjusted by altering the circuitry or software to the needs of the system. By combining noise reduction techniques with signal enhancement techniques like those of an amplifier, which increases the amplitude of the signal, one can produce a more comprehensive signal for analysis.

In general, in addition to detecting, measuring, sensing, and deriving information specifically about electrical signals occurring at nerves, some implementations and aspects of the technologies that we describe here can instead or also use electrical signals occurring in muscle or other tissues. Also, information provided by other sensors or other sources can also be used in combination with nerve electrical signals, including information from inertial measurement units (IMUs), gyroscopes, moisture sensors, temperature sensors, visible light sensors, infrared sensors, cameras, audio sensors, proximity sensors, ultrasound sensors, haptics, skin impedance pressure sensors, electromagnetic interference, touch capacitance, external devices or other detectors.

HMI Platform

As shown in FIG. 9, some implementations of the technologies that we describe here provide a comprehensive, integrated, universal human machine interface (HMI) platform 10 that, on one hand, can detect or otherwise receive and send signals, commands, or other information 12 to and from user interface devices 14 (such as the wrist device) associated with users 16, and, on the other hand, can send and receive signals, commands, or other information 18 to and from application devices and processes 20. Among other things, the HMI platform 10 can accumulate, analyze, alter, and otherwise process the information 12 and the information 18 in a wide variety of ways in order to create a useful comprehensive way for the users 16 to interact through the user interface devices 14 with (we use the term "interact with" in its broadest sense) the application devices and processes 20.

The user interface devices 14 can comprise a wide variety of components including any kind of hardware or software 22 that can receive, process, and send signals or commands or other information from any part of the human body, such as from the fingers, hands, feet, legs, mouth, or eyes, or provide signals or commands or sensory stimulation or other information to any of the sensory organs of the body, including the eyes, ears, nose, mouth, and skin. In some cases, the received information will have been provided as a result of motion of one of these parts of the human body, for example, by motion of a finger or movement of an eye. Typically, the information provided to the user will be provided in a visual, auditory, or haptic form, although other modes are also possible. In some cases, the user interface devices are in physical contact with one or more parts of the user. In some cases, the user interface devices (such as cameras or microphones) are not in physical contact with one or more parts of the user but are able to perceive one or more parts of the user at an appropriate distance.

Among the broad range of kinds of user interface devices 14 that can be served by the HMI platform 10 are keyboards, mice, track balls, joysticks, triggers, switches, touchscreens, dials, knobs, microphones, image sensors, cameras, glasses, headsets, gloves, items of clothing, speakers, earphones, displays, projectors, capacitance sensors, touch sensors, fingerprint detectors, moisture detectors, temperature detectors, motion tracking sensors, ultrasound sensors, phones, smartwatches, laptops, tablets, computers, televisions, vehicles, robots, exoskeletons, prosthetics, drones, health monitoring devices, health monitoring suits, electro-diagnostic systems, alarm systems, and—of particular interest to the discussion of certain examples below—electrodes or other skin electrical potential detectors.

The demarcation between the HMI platform and the user interface devices and between the HMI platform and the applications need not be rigid or static. In some implementations, one or more of the user interface devices (or parts of them) can conceptually be considered part of the HMI platform if the user interface device is specially designed to work effectively with the HMI platform or can be considered conceptually external to the HMI platform if it was not specially designed to work with the HMI platform. In some cases, a user interface device can have elements that are internal to (part of) the HMI platform and other elements that are external to (not part of) the HMI platform. For example, a wristband that detects raw electrical potential signals on the surface of the skin could be conceptually external to the HMI platform, while a signal processor for the electrical potential signals could be conceptually part of the HMI platform even though located on the wrist device.

The signals or commands or other information provided or received by a given user interface device could have resulted from various different levels of processing and combinations of them. For example, the signals or commands or other information could be raw electrical potentials, processed electrical potentials, or higher-level information representative of or derived from the processed electrical potentials or combinations of them. The processing may have occurred entirely in the HMI platform, entirely in the user interface device, entirely in the application devices and processes, or could be split among them in a variety of ways.

Typically, when a user takes an action with respect to one or more of the user interface devices (we use the phrase "takes an action" in its broadest sense), the user has an intent (for example, an intention to click the left mouse button). The intent is developed in the brain and expressed in a gesture (for example, contracting the right index finger—the gesture—to cause the mouse button to be clicked—the intention) and the brain sends signals to nerves that propagate them to the hand to perform the muscle actions (we use the phrase "muscle actions" broadly) that correspond to the gesture.

We use the term "gesture" broadly to include, for example, any muscle action or (frequently) a suite of muscle actions that correspond (alone or with one or more other gestures at a given time or a sequence of times) to one or more intentions of a subject. "Thumbs up", "high five", a "hand shake", clicking a mouse button, flexing an upper arm, and object dragging on a user interface are a few examples of gestures. Gestures can be well known and accepted as part of typical normal human activity or gestures can be newly developed for a variety of purposes. A hand shake is a centuries old gesture, while a mouse click was created as a gesture relatively recently.

An important activity of components of the HMI platform is to identify (infer, determine) gestures 24 (using a gesture identification component 26) and provide information about the gestures through a communication component 28 to the application devices and processes 20 where they can be used in a wide variety of ways. In some cases, the application devices and processes 20 use the gesture information to infer the user's intent and then act on that intent. In some cases, an intention identification component 30 of the HMI platform can infer (determine, identify) a user's intent 32 for example, from one or a combination or sequence of gestures occurring at a moment in time or in a sequence over time, and provide the intention information through the communication component 28 to the application devices and processes 20.

In some cases, the gesture or intent determined by the HMI platform need not be "pushed" to a particular application. The HMI platform can temporarily store the gesture or intent information and provide an API or other mode of making available to any other process, program, or application that may request the gesture or intent information. In that sense, the HMI platform can operate as a service provider, in some cases through an operating system. For example, if the HMI platform is implemented as an app on a smart phone, the app can make available the gesture or intent information upon request to any other authorized app running on the smart phone.

In some examples, the flow of information from the user interface devices to the application devices and processes begins with the brain 52 of a user formulating an intention 54 to take an action with respect to one of the user interface devices 14 or with respect to one of the application devices and processes 20 or both. The brain 52 converts the intention into a gesture (or two or more gestures at a given time or sequence of times) 24 that often involves moving one or more muscles 56 in a way to implement the gesture and in turn express the intention. In some cases, the brain causes appropriate nerves 58 to propagate signals 57 to appropriate muscles to cause them to move in ways that correspond to the gesture. One or more aspects of the gesture can be detected by the user interface devices. For example, the user interface device can be a wrist device having electrodes to detect electrical potentials on the surface of the user's skin that correspond to the electrical signals propagated along the nerves. In some instances, the user interface devices detect the muscle motions in other ways, such as by camera or inertial measurement units. The electrical signals or other events for a gesture as detected by the user interface devices can occur at a moment in time or a sequence of such moments.

The electrical potentials appearing on the skin, or other indications or information about muscle motion, are acquired, sensed, or otherwise detected at the user interface device by one or more detectors 64. Typically, the raw electrical potentials or other indications of muscle motion 65 must be processed (e.g., in a signal processor 66) to, for example, remove noise, remove signals that are not useful, organize and order the signals, and express resulting processed signals in formats that will be useful for the next steps. Other major functions of the signal processor include but are not limited to, measuring, filtering, or compressing, analog signals that are generated as the output of the user (in signal form) for the input of the device.

We use the term "signal processing" broadly to include, for example, any operations performed on relatively raw signals to produce relatively more processed signals that are more accurate, concise, precise, compact, complete, relevant, or understandable, among other things.

The resulting processed signals 68 can then be stored in a storage 70 and (whether or not first stored) sent to the HMI platform by a communication component 72. In the HMI platform, the processed signals can be used by the gesture identification component or the intent identification component to identify corresponding gestures or intent or both of the user. In some cases, the gesture identification component and the intent identification component can be combined as a single component. In some instances, one or the other of them need not be included. In some implementations, the two components can operate in parallel.

The gesture identification component and the intent identification component can receive and use combinations of processed signals from two or more different user interface devices or detectors and can apply one or more algorithms, analytics, transformations, or other interpretation processes to interpret, identify, or determine the gestures and intent of one or more users.

A wide variety of gesture or intent identification processes representing a range of different complexities and styles can be used. In some cases, the identification process can be as simple as determining that an electrical switch in a computer mouse has made contact and identifying that the user's gesture was to click the mouse button. In some instances, the identification process can be a more complicated method needed to interpret, for example, a set of nerve electrical signals detected on the surface of the skin of the wrist of the user. Classifiers or other machine learning components can be used in such cases. Basic machine learning algorithms like Fine Gaussian support vector machines (SVMs) when trained on a representative feature set are able to achieve high accuracy while maintaining low computational complexity. As more user data is aggregated, the accuracy of the model will increase if the feature set is representative of the actions being distinguished from one another. If the extracted feature set is not representative or does not increase in accuracy more computationally intensive learning frameworks can be used to identify features. Deep neural nets have been shown to be effective in identifying a concise and representative feature set. However, this feature set may not rely on the underlying biology and may reduce the ability to make inferences about the system. By training such machine learning processes based on known relationships between nerve electrical signals and corresponding gestures or intent, it is possible to apply the trained process at "run time" to a new set of nerve electrical systems from a user to derive a correct interpretation of a corresponding gesture or intent of the user. As mentioned earlier, in some cases, features of a feature set are extracted from known data and correlated with known gestures as the basis for training and then applying the machine learning techniques.

As mentioned earlier, in some implementations, the HMI platform includes one or more intent identification components that can use the identified gestures or other processed signals or both to infer the intent of the user that corresponds to one or more gestures. Machine learning techniques can be used for this purpose. For example, a gesture identification component may determine that processed electrical signals correspond to a gesture in which the user is waving his hand in the air with his index figure extended, and the intent identification component could use that interpreted gesture to infer the intent of the user to be picked up by a taxi.

The HMI platform can serve a single user interface device of a single user (e.g., a wrist device) and a single application device or process of the user (e.g., augmented reality glasses), or it can serve multiple user interface devices, multiple users, multiple application devices or processes, or combinations of them. For example, a user may have a wrist device and a track ball as user interface devices and a smart phone and a laptop computer as applications.

Communications between the HMI platform and each of the user interface devices and each of the application devices and processes can conform to agreed protocols and formats for the signals or other information being communicated. In some implementations, the HMI platform is custom-configured to communicate using protocols and formats that are peculiar to a user interface device or an application device or process being served. In some instances, the HMI platform can communicate using protocols and formats that are device-independent and process-independent and can serve essentially any user interface device or any application device or process that conforms to the protocol or format independently of its design or manufacture. For this purpose, components of the HMI platform can expose one or more application programming interfaces (APIs) or both to user interface devices or application devices and processes. In some cases, the APIs can define standardized formats and data structures to be used to express signals or commands or other information that are passed back and forth between the HMI platform and the user interface devices or the application devices and processes. (For simplicity, we sometimes will use the word "application" to refer broadly to any such device or process.)

Wrist Device

As shown in FIG. 10, some examples of user interface devices are in the form of a wrist device 802. The wrist device can include, for example, a generally rigid component 804 connected to a flexible, adjustable wrist band 806 configured to permit the inner circumference 809 of the wrist device to be adjusted to different size wrists much as a watch band can be adjusted to the wrist of its user.

In some implementations, the rigid component 804 includes a housing 806 on which are mounted a circuit board 808 holding electronic components, a battery 810, a user interface panel 812, a communication (e.g., USB) port 814, an external electrode port 816, (e.g., quick release) wrist band mounting pins 818, 820 to lie within channels of the wrist band, and a set of electrodes 826 held in an electrode cartridge 822.

The housing 806 is generally configured to rest on the top of the wrist with the wrist band wrapped around the bottom of the wrist. The housing is designed to provide a rigid inner surface 828 having two segments 830, 832 that cooperate to keep the wrist device registered in a predefined position and orientation with respect to the relatively flat top surface 834 of the wrist and to the outer side 836 of the wrist along the side of the ulna, and also registered against the styloid process 838 of the ulna. As a result, although the wrist device can be worn on many different sizes and shapes of wrists, it will reliably be in a known position and orientation to detect electric potentials at the upper surface of the wrist produced by electrical signals in the ulnar nerve and the median nerve. This is because the ulnar and median nerves tend to be positioned at roughly the same distance from the side of the ulna for wrists of many different sizes and shapes. Consequently, the electrodes (described later) that are exposed at fixed positions at the rigid inner surface will reliably detect electric potentials at the skin that are generated by known nerves in the wrist.

To achieve this automatic registration on wrists of various sizes and shapes, the segment 830 has a flat rigid inner surface 840 and the segment 832 has a concave curved rigid inner surface 842 that meets the flat rigid inner surface. The contours of inner surfaces 840 and 842 tend to urge the wrist device into a consistent position and orientation relative to predetermined locations along the nerves that control the hand muscles for wrists that have a variety of sizes and shapes.

The electrodes 826 are exposed at the rigid inner surfaces 840, 842 so that contact surfaces 844 of the electrodes face the skin of the wrist. A wide variety of sizes and shapes of contact surfaces 844 are possible. In some cases, the contact surfaces are round and can have widths in a range as small as one millimeter (or smaller, in some examples) or as large as ten millimeters (or larger, in some instances). Typically, the contact surfaces will be flat but other contours may be useful to match contours of the skin, for example. Different ones of the electrodes can have different sizes and contours.

In some implementations, the contact surfaces are arranged in a pattern. The pattern can comprise pairs 846. In some cases, each pair can be positioned along an axis 848 that is parallel to the length of the forearm with one electrode of the pair closer to the fingers than the other electrode of the pair. The number of contact surfaces can be as few as two and as many as tens or hundreds. In particular implementations, there can be between two and eight pairs of the contact surfaces arranged in a series along the rigid inner surface. The spacing between the two contact surfaces of each pair can vary; in some cases, the spacing could be in a range as small as five millimeters or as large as 25 millimeters or more. The spacings between adjacent pairs of electrodes can vary.

A wide variety of other patterns of electrodes and their contact surfaces can be used including patterns of regular rows and columns and patterns that are irregular along either or both of two dimensions.

In some implementations, some of the electrodes can have contact surfaces exposed on the inner surface of the flexible wristband 806 for contact with other parts of the skin of the wrist, including the bottom of the wrist. Such electrodes can be organized in pairs in regular rows and columns or in other patterns and can number as few as one electrode or as many as tens or hundreds. The contact surfaces can have various sizes, shapes, dimensions, and contours as indicated for the contact surfaces described above.

In general, the numbers, sizes, shapes, contours, and patterns of organization of the electrodes can be chosen empirically, for example, to provide the most accurate, concise, precise, strongest, and least noise-influenced electrical potential signals from the skin of the wrist and to provide the most accurate inferences from such potential signals of contractions or relaxations of particular muscles, gestures, and intent.

By using a very large number of closely spaced electrodes to capture electrical potentials from a closely spaced array of locations on the surface of the skin at a given body part over time, it can be possible to derive accurate information about the action potentials of (every) nerve, and muscle in the vicinity of the measuring electrodes over time. That information can be useful for a variety of purposes.

For purposes of carrying electrical current from the contact surface of each of the electrodes to the signal processor 66 wires, conductive runs, or other types of electrical couplings are provided between the electrodes and circuit board 808. Typically, each of the electrodes will have its own such electrical connection so that the electrical potential on that electrode can be detected and measured independently of the electrical potential on any of the other electrodes. In some cases, two or more of the electrodes can be connected through a common electrical connection to the circuit board. As shown in FIGS. 12, 13, and 14, each of the electrodes can include a snap nipple 841 on the opposite face of the electrode from the contact surface 844. The snap nipple mates with a snap socket 843. The snap socket is mounted loosely in a sleeve 845 of the electrode cartridge to be slidable along the axis of the socket. A helical spring 847 is soldered to the snap socket.

Any one or more of the electrodes can be mounted on or at the rigid inner surface of the housing or the inner surface of the flexible wrist band. One or more of the electrodes can be mounted to be resiliently urged toward the skin when the wrist device is worn. As shown in FIGS. 12, 13, and 14, in some cases, the resiliency of an electrode can be achieved by mounting it in the sleeve 845 in the cartridge 822 and incorporating the helical spring 847 to urge the contact surface of the electrode in the direction of the skin. The direction in which the resiliently mounted electrode is typically urged is normal to the inner surface of the wrist device but could be in a non-normal direction. The span of the motion of each of the resilient electrodes can be in the range of from, say, one millimeter or less to five millimeters or more.

As a result of these features, when the wrist device is put onto the wrist each of the resiliently mounted electrodes will automatically form a good electrical contact with the skin and will accommodate small differences in the distances between the inner surfaces of the wrist device and the skin of the wrist at various locations.

Other configurations can be used for the wrist device and its components to achieve resiliency of the electrodes. For example, the housing or a portion of the housing (for example the portion that faces the skin) can be formed of a flexible resilient material (such as rubber) and the electrodes can be mounted directly in that material with a short section of the electrode projecting from the inner surface toward the skin. When the wrist device is put onto the wrist, the flexible resilient material urges the contact surfaces of the electrodes toward the skin to continuously provide good contact with the skin when motion of the wrist, for example, causes small changes in the small gap between the surface of the skin and the inner surface of the housing.

As noted above, in some cases, the electrodes can be attached to and detached from the wrist device using a snap to permit easy replacement. In some implementations, mounting of the electrodes can use disk magnets embedded in the inner surface of the wrist device, a flexible circuit with connection runs is embedded within the wrist device, and the electrodes fit within divots provided in the inner surface of the wrist device and have magnets to couple to the disk magnets.

The electrodes can be formed of a variety of metals, metal alloys, or conductive materials, but certain ones are more effective than others. Regarding metal and metal alloy, silvers, coppers, golds, aluminums, zincs, nickels, and brasses are several of the more conductive ones. Electrodes formed with these materials work especially well because their electrons move more freely than that of other elements or alloys. This causes any electrical current exhibited on these materials to travel with little resistance. Some other conductive materials and compounds include silver/silver chloride (Ag/AgCl), conductive fabrics and threads, and graphene. In some implementations, the electrodes are used in a dry contact mode in which the contact is made directly between the metal of the electrode and the skin. Conventional dry contact electrodes tend to produce high impedance coupling between the electrodes and the skin, which makes it difficult to acquire good electrical potential signals. This issue is addressed in wet electrode technology by providing a liquid or gel conductive material that produces a low impedance coupling to the skin, but has the disadvantage of being messy, among others. Some implementations of dry electrodes that we describe here use a conductive gel and a permeable membrane that permits exchange of ions between the skin and the conductive gel while blocking moisture from wetting the outside of the membrane. Such electrodes are described in U.S. Pat. No. 8,798,710 (the contents of which are incorporated here by reference) and are available from Cognionics of San Diego, Calif., USA.

In some examples, one or more of the electrodes can be mounted rigidly without resilience.

In some cases, the registration of the wrist device on wrists of different sizes and shapes can be achieved by techniques other than rigid features. For example, housing structures with flexible joints, hinges, or modular components can accommodate different wrist sizes and shapes. The device could have elements for resizing like an adjustable wrench, like a clamp, or like a clam-shell. Segments or lengths of the housing could be added or removed to extend or reduce the overall size of the housing as in linkages of a watch.

Through the external electrode port 816, a wire 817 can be connected from the housing 206 to an external "stick-on" electrode 856 that can be attached to the skin of a subject by tape or other adhesive techniques. The external electrode 856 can be of the kind that uses the permeable membrane. In some cases, the external electrode can be applied using a conventional conductive liquid or gel.

The port 816 could be arranged to provide independent connections to two or more such external electrodes.

In some cases, the external electrode or electrodes can be used in similar ways and for similar purposes to the electrodes mounted on the wrist device. In some cases, the external electrode or electrodes can be used in different ways and for different purposes. For example, the external electrode could be placed in a position or orientation to detect muscle electrical signals that could be used to offset or cancel muscle electrical signal noise in one or more other electrodes. In some instances, the external electrode or electrode can be used for experimental or study purposes.

The USB port 814 can receive a USB connector 815 for purposes of communicating data, information, and commands between the wrist device and, for example, the HMI platform, and to carry current to charge the battery in the wrist device.

The circuit board 808 can take a variety of forms, shapes, or sizes that are consistent with the mounting of the wrist band on a wrist. Electronic components can be mounted on the circuit board.

As shown in FIG. 16, in some implementations the electronic components on the circuit board of the wrist device include analog components 860, digital components 862, and one or more analog-to-digital converters 864 that convert analog signals that are captured by the electrodes processed by the analog components for delivery to the digital components (e.g., one or more digital processors 866) for further digital processing.

The processor 866 uses digital signal values 868 received from the one or more analog-to-digital converters. The digital signal values are based on electrical potentials at the respective electrodes at moments in time and sequences of moments in time.

In some implementations, the digital signal values represent differential potentials, that is, the difference between the electrical potential at one electrode 873 and the electrical potential at a second electrode 875, both relative to a ground potential at a third electrode 877.

For this purpose, the two electrodes of each differential pair can be connected to and served by a dedicated signal path 870, 872 from the electrodes to a shared analog-to-digital converter 864.

Each of the digital signal paths includes a notch filter 874, 876 that removes, for example, 60 Hz frequency components of the electrical potential signals detected at the skin by the two electrodes of the differential pair, to reduce or eliminate the noise caused by 60 Hz power sources in the vicinity of the subject. The notch-filtered version 878 of each electrical potential signal is delivered to an instrumentation amplifier 879 the output of which is the value of the difference of the electrical potentials at the two electrodes of the differential pair. In determining the difference of the electrical potentials, each of the electrical potentials is considered relative to a common ground potential represented by the electrical potential at a third particular electrode that is typically selected to be away from the locations on the wrist where good electrical potentials from nerve electrical signals can be detected. Therefore, the difference of the electric potentials is the difference of two values, one being the difference between the electrical potential at one of the two signal electrodes and the electrical potential at the ground electrode, and the other being the difference between the potential at the other of the two signal electrodes and the electrical potential at the same ground electrode. In some implementations, the ground electrode is pre-selected and cannot be changed. In some cases, any of the electrodes can be selected as the ground electrode 877.

Similarly, in some cases, the processor can select which electrodes comprise each of the differential pairs of electrodes and which of the pairs are being actively used (polled) by the processor at a given time. In the case of multiple processing channels, one channel could receive electrical potentials from a specific three of six available electrodes; the other channel could be switchable between the stick-on electrode (connected to the audio jack) or one of the electrodes having a contact surface exposed from the inner surface of the wrist device. By utilizing multiple channels there is more access to raw signal information as the data is collected from each corresponding set of electrodes. This data can be processed and utilized for discerning more complex gestures, collecting data for research studies, comprehensive disambiguation of muscular or nerve signals as well as other applications.

The gain of the instrumentation amplifier is governed by a programmable resistor 880, the gain of which is controlled by the processor. This dynamic gain of the instrumentation amplifier provides an impedance matching function to match the impedance between the two electrodes of the differential pair. The instrumentation amplifier is also connected to ground by virtue of the third electrode 877.

As shown in FIG. 19, dynamic impedance matching of the instrumentation amplifier 980 to the changing impedance of the electrode-skin interface 982 helps to improve the signal-to-noise ratio of the signals acquired from the electrode. A dynamic impedance matching component 984 receives measurements 986 of the impedance of the electro-skin interface. The impedance measurements are done by a measuring component 986. Based on the impedance measurements, the dynamic impedance matching component calculates an ideal resistance (impedance) of the instrumentation amplifier input needed to improve (e.g., maximize) the signal-to-noise ratio. An output 988 of the dynamic impedance matching component 984 then controls the resistance of the programmable resistor 880 accordingly.

The output of the instrumentation amplifier, the differential potential value 882, is provided to a band pass filter 884, which passes a band of frequency components of the differential potential value that are characteristic of electrical signals appearing at a kind of tissue of interest. In some examples, the tissue of interest is nerve tissue and the band pass filter can pass signal frequency components in the band 20 Hz to 1000 Hz, which removes some frequency components characteristic of tissues that are not of interest. For example, muscle electrical signals typically have frequencies in the range of 5-400 Hz, nerves have frequencies in the range of 200-1000 Hz, including brain electrical signals (the frequency of individual neurons firing, rather than EEG brain waves (alpha, beta, gamma) which are the lower frequency (0 Hz to 80 Hz) oscillation patterns of aggregated nerves.

The band-filtered version of the differential signal 886 is provided to a gain amplifier 888 in its original form 890 and also to the gain amplifier in a rectified form 892 after having been passed through a rectifier 895. The gain amplifier uses as its input the original signal if it has a positive polarity and the rectified form if the original signal has a negative polarity. The gain of the gain amplifier is controlled by the value of a programmable resistor 894, the value of which is determined by the processor. The processor determines this gain level based on the output signal voltage. Outputting the signal this way provides data at a measurable voltage level for easier visualization and analysis.

When a propagated electrical signal (action potential) appears at a location along a nerve, electrodes that are closer to that location will detect a higher electrical potential on the skin than electrodes that are farther away. When a propagated electrical signal (action potential) appears at a location along a nerve, a polarization phase occurs and the electrical potential changes when reaching a threshold. The electrical potential moves towards a positive orientation. Then, as the action potential at that location goes from an excited state to a resting state, during a so-called repolarization phase, the electrical potential will go to zero and swing briefly to a refractory period, or a more negative potential than its initial state, before converging at a resting state. The electronic components take advantage of this effect to determine the direction of propagation of the action potential in order to disambiguate motor action potentials from sensory action potentials, and to determine the speed of propagation.

The analog-to-digital converter is continually receiving processed versions of the differential electrical potentials detected at each of the differential pairs of electrodes on the skin. The analog-to-digital converter is controlled to sample only one of the differential electrical potentials from one of the pairs of electrodes at a given time and to sample the different pairs of electrodes in, for example, a round-robin mode. The analog-to-digital converter can be arranged to sample input signals at any rate that is high enough to capture frequency domain information of interest carried by each of the input signals and to capture that information for as many differential pairs of electrodes that are served by the analog-to-digital converter. In two specific examples, the rate of polling a differential pair of electrodes could be 500 Hz or 4000 Hz or higher depending on the specifications and limitations of the analog-digital converter. One analog-digital converter can serve one differential pair of electrodes or many, in which case the sampling rate of the analog-digital converter would be shared among the pairs. The polling rate should typically be at least twice the frequency of the signal being detected. In some implementations, more than one analog-to-digital converter could be used to serve corresponding sets of electrode pairs in parallel.

In typical implementations, therefore, the processor (we sometimes use the singular "processor" to refer also to examples that use two or more "processors" in parallel, for instance) will receive streams of digital potential values representing differential electrical potentials at the respective differential pairs of electrodes at successive moments in time. In some cases, the processor is a special purpose processor that serves as a characterization engine to characterize motions, gestures, or intent based on the digital potential values. We sometimes use the term "processor" to refer to such special purpose processors or characterization engines.

Each digital potential value can be, for example, a 24-bit value (if the analog-to-digital converter has a 24-bit resolution) tagged with an identifier 902 to associate it with one of the differential pairs of electrodes and also tagged with a time stamp 904.

In addition to receiving and using the digital potential values provided by the analog-to-digital converter, the processor can receive and use other digital source values 905 received from a wide variety of other input sources 907, such as 9-axis or other inertial measurement units (IMUs), gyroscopes, moisture sensors, temperature sensors, light sensors, cameras, audio sensors, location sensors, and proximity sensors, to name a few. The IMU can provide data about a user interface device being tapped or jostled either by the user as an intentional or unintentional input which can be used as a digital source value. One or more of these digital source values can be used by the processor in implementing processes that generate the characterizations mentioned earlier.

The incoming digital potential values and the incoming digital source values (we sometimes use the term "digital values" to refer to both the digital potential values and the digital source values) can be stored temporarily in memory 906 mounted on the circuit board. The storage can be of a size that is large enough to serve as a buffer but not to store large volumes of digital values for study or later use. In some cases, the storage can be large enough to temporarily store a substantial volume of digital potential values during periods when the wrist device cannot communicate with other parts of the HMI platform, for later communication to the HMI platform. In some instances, the storage can be large enough to store an entire set of digital values to be used by the processor or by other parts of the HMI for a particular task. Portions or all of the stored digital values can be transferred wirelessly by the wrist device to other parts of the HMI, such as to a local smart phone as needed. Bluetooth or any other wireless protocol can be used.

The processor on the wrist device can process the digital values essentially in real time as they are detected, or by fetching them from memory as needed, to produce characterizations 908 of muscle contractions or relaxations, gestures, or intent, or combinations of any of them. We use the term "characterization" broadly to include, for example, the digital potential values themselves, translations or modifications of them, and any identifications, descriptions, inferences, or other indications or quantifications of muscle contractions or relaxations, gestures, or intent or combinations of them. After processing the digital potential values, the resulting characterizations can be stored in the storage on the wrist device, or communicated to another component or portion of the HMI, for example, to one or more applications or for any of a wide variety of other purposes.

As one specific example, a particular set of digital values can be processed by the processor to generate one or more characterizations of a contraction of the index finger of a user corresponding to a motion used to click a button of a mouse. The characterization of the gesture can be sent wirelessly essentially in real time to a local computer running an interactive application where the characterization can be treated as a mouse click event even though the user has only engaged in a mouse click gesture but has not actually clicked a physical mouse button.

In some cases, the characterizations can represent quantifications of specific two-dimensional or three-dimensional positions or orientations or changes in position or orientation of a part of the body of the user, for example, a tip of a finger. Because of the accuracy, precision, and quality of the digital potential values, the quantifications can be more precise than known other techniques and may be, for example, at a resolution of one millimeter or smaller. The accuracy of the quantification can be affected by the size of nerves, the size of muscles, and the size of electrodes. In some cases, the resolution may be in the range of ten millimeters.

The processor can use a wide variety of algorithms, techniques, computations, translations, mappings, transformations, classifiers, statistics, models, analyses, or other processes and combinations of them to generate the characterizations from the digital values. The processes used can depend on the processing power of the processor, the storage capacity of the memory, the number, type, and rate of receipt of the input digital values, the complexity of the characterizations to be generated, and other factors. The processes and portions of them can be implemented in a variety of ways, including as software executed by a special purpose processor, as firmware, or as dedicated hardware. In the case of software or firmware, the processes or portions of them can be installed at the time of manufacturer or can be installed or updated after manufacture, for example, by a wireless download or a wired download through the communication port (e.g., a USB port). Such updates can improve or otherwise alter the performance and operation of the processes or portions of them based on knowledge developed over time (for example using historical data about the correlation of electrical potentials and corresponding characterizations), can take account of new and additional data sources available to the processor, and can serve new or additional applications.

In a relatively simple example, the processor could perform the following steps to generate a characterization of a gesture based on 24-bit digital potential values from the analog-to-digital converter. The $2^{24}$ possible digital potential values can be classified using three threshold states (LT [construed as the hand at rest], MT, and HT), and the classifications can be used to derive a characterization of a gesture as follows. A sequence of a digital potential value going above LT and later falling below LT is characterized as gesture 1; a sequence of a digital potential value going above MT and later falling below LT is characterized as gesture 2; and a sequence of a digital potential value going above HT and then falling below LT is characterized as gesture 3.

In some cases, two or more digital potential values can be used to characterize a gesture. For example: a sequence of digital potential value 1 going above LT and digital potential value 2 going above LT and then digital potential value 1 going down to LT is characterized as gesture 1; a sequence of digital potential value 1 going above LT and digital potential value 2 going above MT and then digital potential value 1 going down to LT is classified as gesture 2; a sequence of the digital potential value 1 going above LT and digital potential value 2 going above HT and then digital potential value 1 going down to LT is classified as gesture 3; and a sequence of digital potential value 1 going above MT and digital potential value 2 going above LT and then digital potential value 1 going down to LT is characterized as gesture 4. LT, MT, and HT are the values being compared to a low threshold, mid/medium threshold, or high threshold value in order to understand the correlation between a motion and the amplitude of the motion.)

If sufficient processing power is available, more complicated sets of gestures (and intent) can be determined from more complicated sets of digital potential values and sequences.

In some processing-intensive examples, the processor executes a classifier process 910. The classifier process and classifier data 912 used by the classifier process are loaded either at the time of manufacture or later. In some cases, the classifier data identifies (a) sets of sources of digital values (such as a set of digital values from particular electrodes or specified IMUs), (b) specific digital values or ranges of those digital values (the sets of sources and the specific values or ranges of values are sometimes referred to as "feature sets") and (c) corresponding characterizations (such as muscle contractions or relaxations, gestures, or intent) that are known to be correlated to the feature sets. In effect, the classifier captures information about which feature sets correlate to which characterizations. At "run time" the classifier process tests incoming sets of digital values and sequences of them according to the classifier data, and maps them to corresponding output characterizations and sequences of them based on the classifier data. The output characterizations and sequences of them can be stored or forwarded to applications or parts of the HMI for a wide variety purposes.

Other types of characterization processes can be used. For example, frequency domain analysis can be used to characterize different actions that are performed, due to the different frequencies in the biopotentials. Common average reference (CAR) can also be used to characterize different actions when multiple electrodes are in place. Simply by comparing one electrode with the average of all the electrodes around the wrist to characterize activation base on the electrode location. Small and large Laplacians can be used to characterize the action by comparing the sum of the nearest electrodes to characterize the actions.

The wrist device has an outer surface that provides a user interface panel 812 for interaction by the user. As shown in FIG. 15, in some examples, the user interface panel includes two buttons 823 and 825. The function of button 823 is to control the power of the device, either on or off. The function of button 825 is to provide Bluetooth pairing control and to turn the Bluetooth controller on or off. An LED 827 between the two buttons provides the following functions: indicates status of the device including power on, Bluetooth pairing, as well as visual feedback of sensor data including neuromuscular signal amplitude, 1MU, haptics, and sensor fusion when combining data from multiple sensors.

In some examples, the user interface panel is a touch sensitive OLED panel that allows for visualization of data values and characterizations and input features such as a keyboard. The panel can display the ranges of information that a smartwatch, phone, smart glasses, and computer would. The panel can provide data such as charting, menu selections, mode changes, status of device operation, pairing status, battery life, videos, apps, internet sites, and content from tethered devices such as smart glasses or phones, and general computing. The user can interact with the OLED in the same methods as those used by smartwatches, phones, smart glasses, and computers including tap, touch, swiping, or sliding one or more fingers or stylus.

The OLED panel will enable the device to have a low power display and have readability in sunlight with a higher quality illumination. Flexible display panels can be used to provide less rigid design options.

For purposes of enabling a developer to create software, hardware, and firmware for use by the processor of the wrist device, a developer's kit can be provided in connection with the wrist device. The developer kit enables the user to define what data values will be stored on the wrist device, for how long, and in what format; when and how the data values will be delivered to other parts of the HMI, what processes will be used to derive characterizations from the digital values, and how the characterizations will be expressed. The developer's kit can also enable the developer to define analytics to be applied to the data values and to the characterizations by components of the HMI, to define elements of a user interface to be presented to the user on the wrist device, and to specifically define mappings between features sets and corresponding characterizations.

In some cases, the wrist device can contain or be combined with other functions or features such as those provided by a watch, or a smart watch, or an exercise monitor, or a health monitor that monitors or provides feedback with respect to pulse rate, blood pressure, temperature, skin moisture, humidity, barometric pressure, acceleration, inertia, orientation, skin pressure, blood oxygenation levels, or other parameters. In some cases, these functions can operate independently of the functions related to tissue electrical signals. In some implementations, the functions can be combined or the data generated by such functions can be used as additional data sources for the processor in the user interface device.

App

As shown in FIG. 17, in some cases, one or more features of the HMI platform can be implemented in an app 926 running on a smart phone, tablet, laptop, or other processing device 928, for example. In some cases, these features can be implemented in a processor that is part of the wrist device. In some instances, the features can be implemented in a combination of the user interface device and the HMI platform.

The features 930 can be implemented in hardware, firmware, or software, or combinations of them. Each feature can be implemented by a module. In general, the features can involve user interaction through a user interface 932 of the device 928 and can enable the user to customize, control, modify, configure, invoke, terminate, and otherwise use each of the features.

One of the feature modules can enable a user to create or customize gestures that the gesture identification component can identify. For example, the user can define a new gesture by instructing a gesture customization module 934 to accept a new gesture and then performing the gesture. As the gesture is performed, the data values from the processor in, for example, the wrist device are collected and stored and associated with the gesture being defined. The user can then associate the defined gesture with an action to be taken by other apps when they receive an indication that the gesture has been performed. For example, the new gesture could be the making of a fist, and the user could cause this gesture to be associated with the command to close the target application. The user could be prompted to perform the gesture a number of times so that additional sets of data values associated with that gesture can be stored and, say, used to train a classifier. The gesture customization module also could be used to update or modify an existing gesture, for example, by enabling the user to update the action to be taken by the target app when the gesture is identified or to classify slightly different physical motions as representing the gesture (say making of a hard first versus gently closing the hand).

One of the feature modules can be an outcome customization module 936 that enables a user to identify the action to be taken by the target application with respect to any existing or newly created gesture. For example, if the gesture is the closing of the index finger, the action to be taken could be clicking a mouse button, typing a character, or another action, as determined by the user through a user interface presented by the outcome customization module.

One of the feature modules can be a communication module 938 that translates gestures into corresponding communications so that a user can communicate through a variety of apps without using a keyboard or voice as is typically done. The communication module can accept gestures from the gesture identification component and generate corresponding communications or elements of them for use by another app such as a texting app, a word processing app, a speech synthesis app, or a social networking app, for example. The mapping of gestures to communications can be based on a standardized pre-defined set of relationships. In some cases, the user can view, update, or modify the mappings or create new mappings through a user interface presented by the communication module.

One of the feature modules can be a biopotential tracking and monitoring module that translates the electrical signals generated into an output visualization. This visualization would show, in some cases, the frequency and amplitude data produced by the user in a graph-like manner. This visualization would update over the period of use of the device. For example, a patient with a degenerative muscular disorder would wear the device and be able to monitor their signal output over time alongside their clinician. In some cases, the user can view, move, or update the graphs manually through a user interface.

One of the feature modules can be body composition analysis module. Fat and water have different impedances when exposed to an electrical current. Lean tissue is mostly water and has a much lower impedance than fatty tissue. This allows the measurement of fat content and water content in the body along with further health metrics. For example, if a small amount of current is sent through one electrode in the wrist mounted device to the user it can be received at another. It is then possible to calculate an individual's fat free mass and body fat percentage based on the impedance values measured and that individual's height and weight.

One of the feature modules can be an activity tracking module that translates the electrical signals generated into an output visualization. This visualization would show, in some cases, the frequency an individual has activated certain neuromuscular areas and how those activations relate to resting or exercise values in a graph-like manner. This visualization would update over the period of use of the device.

One of the feature modules can be activity identification module in which the device recognizes the activity performed by the user. For example, the user closes their first to a certain point and flexes the forearm and bicep to do a pullup exercise. The device identifies the gesture performed and the orientation of the device relative to the user and corresponds it to that activity.

One of the feature modules can perform object identification based on touch.

One of the feature modules can be a stimulation control module that stimulates the user with an electrical current in order to elicit an action based on a desired setting. Sending current through the device with a variable controllable resistor allows the device to be used for stimulating certain neuromuscular areas for therapeutic and other medical purposes.

Calibration

A calibration process is a step in the use of one or more user interface devices such as the wrist band. The calibration can be physical or electronic (e.g., digital) or a combination of them. Among the goals of the calibration are to improve user placement of, for example, the wrist device (and in turn the electrodes on the wrist device) or to improve the signal-to-noise ratio of the detected electrical potentials or both. In some cases, the user interface will provide on-screen instructions to help the user establish proper calibration of the device. This may also include a short testing phase to ensure activations are being recorded accurately by the device.

For purposes of calibration, it can be useful to provide on a user interface, visualizations of data values, characterizations, or a three-dimensional representation of a body part that moves in response to such characterizations.

Data Sources

Much of the discussion to this point has related to the detection, identification, processing, and use of electrical potentials produced by nerve electrical signals in the wrist. The technology that we describe may be used with respect to nerve electrical signals in other parts of the body, including the brain and other extremities, for example, and can be used for detection identification, processing, and use of electrical potentials produced by other tissues such as muscle tissue. In addition, a wide variety of other data sources can be used by the processer in generating characterizations of gestures, intent, and muscle contractions, among others.

For example, combinations of data values from native infrared cameras, RGB cameras, and LED displays can be used to generate eye gaze data for use in combination with electrical potential information for generating characterizations.

In some implementations, electromyography (EMG) information can be captured at the wrist, for example, along with the nerve electrical signal information. The EMG information can be useful in its own right and as data source to the processor for improving the quality of the data values generated by the processor. The EMG information can be captured by one or more secondary electrodes on a wrist device, for example.

In some cases, other data sources such as IMUs can provide information that can be interpreted along with the data values from the processor to disambiguate gestures and direct interaction with the user interface of a user interface device, for example, to distinguish a user making a gesture in the air from a user touching a control of a user interface of an application. In this sense, more broadly, combining data values from the processor with data from other sources such as IMUs can be helpful in recognizing intent of a user.

There are pathways of electrical activity between the user's brain and the parts of the body (for example, the fingers) that ultimately move as a result of intentions formulated in the brain. The pathways begin in the brain (the site of neurological activity and associated electrical activity that can be measured on the skull) and extend along the nerves (which also exhibit electrical activity along their lengths) to tissues that can include muscles and possibly tendons (where the contractions or relaxations of muscles and associated electrical activity occur). Electrical activity occurs first in the brain and then along the nerves and the muscle contractions and relaxations then happen.

The speed of determining a person's intent and gestures may depend partly on how near to the brain neurological activity measurements are made. The accuracy and robustness of the determinations of intent and gesture may depend on the number and locations of places where measurements are made. For example, although using IMUs to determine the actual motions of the fingers or hand may provide very good information about a gesture, that information is derived after a delay associated with the time required for the brain neurological activity, the propagation of electrical signals along the nerves, the reaction of the muscles, and the processing of the IMU signals. In addition there may be subtle aspects of intent and gesture that cannot be fully determined from IMU signals alone, but only by also measuring and processing nerve signals and brain signals.

In some implementations of the technologies that we describe, measurements are taken not only of nerve electrical activity (say, at the wrist) and of actual motion of parts of the body (for example, using IMUs to measure motion of fingers) but also of nerve electrical activity at places nearer to the brain (e.g., by measurements at the skin along the arm)

and of brain electrical activity (by EEG or similar techniques). Analyzing the relative timing and intensities of electrical signals and finger and hand motion along the pathways and the combinations of these signals and motions can enable richer, more complex, and faster interpretation of intent and gesture, which can be useful for many applications, including gaming, manufacturing, and control of applications.

The technologies that we describe include platforms for the study of the pathways and for developing machine learning and other techniques for interpreting the signals and motions along the pathways. In some cases, it may be possible, by such studies, to correlate brain electrical activity sufficiently accurately to measured signals at the wrist and measured motions of the hand and fingers to enable reliance solely on the brain electrical signals as good indicators of intent and gesture.

Applications

The applications for the technologies that we describe are wide ranging and include industrial, business, consumer, medical, institutional, and military uses, for example. Functionally the applications span a broad range, including monitoring, control, feedback, actuation, communication, and data accumulation and analysis, among others.

Monitoring applications involve detecting, storing, and accumulating data values for tissue electrical signals of individuals and groups and populations of individuals, such as monitoring nerve electrical signals (sometimes referred to as electroneurography or ENG signals), ENG or sENG (surface ENG) signals in combination with EMG or sEMG signals, and monitoring other combinations of EMG, sEMG, ENG, sENG, EEG, ECG, and IMU signals, for example.

Such monitoring can provide bodies of data useful in measuring or analyzing the fitness (in terms of muscular strength or stamina, for example) of groups of subjects or individual subjects, including military personnel. By also using data that represents muscle strength, the monitored bodies of electrical signal data can be used to develop correlations between tissue electrical signals and muscle strength and those correlations can be used to characterize muscle strength based on data values derived from skin electrical potentials, for example.

Monitoring applications can be useful in medical fields. Among such applications are the monitoring of heart rate and EKG from the wrist or foot. The heart generates strong electrical signals in the one millivolt range that can be detected on the surface of the skin on the chest as well as on the appendages. Heart rate signals occur at a frequency that is discernable from other muscle and nerve signals. The importance of tracking heart rate is for determining measures of the user's health or condition. This is also useful because traditional methods to capture heart behavior are possible only on the chest. These neuromuscular sensors that we have described can disambiguate ECG patterns on the entire body including the wrist and foot. Traditional wrist based methods using infrared technology measure only heart rate and not heart behavior such as the timing of the heart chambers. The radial pulse is palpable on the wrist. While pulse can also be measured on the dorsalis pedis and posterior tibial areas of the foot and ankle respectively, among other locations on the body. This gives a multitude of methods and locations to perform an EKG depending on the patient's or physician's needs.

Monitoring the state and progression of neurological disorders such as ALS and other neurodegenerative disorders can also be useful. More generally, any context in which non-invasive accurate monitoring of nerve electrical signals would be useful for diagnosis or therapy or observation of progress of a disease with or without therapy would be susceptible to useful applications. For example, observation of therapeutic outcomes, such as after any surgery that involves or implicates the condition or operation of nerves or muscle or other tissue, may be useful. Monitoring can also be used in diagnosing, quantifying or treating neuromuscular conditions; tracking epileptic activity; monitoring to predict a future state, condition, or change in nerves or muscles; or monitoring and analysis of muscle cramps. Monitoring can be useful in determining trends that are reflected in tissue electrical signals, including muscle deterioration and disease progress.

In some instances, patients can be provided with real time cues and feedback to aid in proper muscle recruitment and movement patterns to improve rehabilitation outcomes. Other applications include limb loss and spinal injury.

When monitoring occurs, the data values can be received, stored, or accumulated not only at the user interface device (such as in the memory of the wrist device) but also in devices (such as smart phones) that are in the vicinity of the user interface device, and more generally in one or more components of the HMI platform, or in one or more of the applications. In some implementations, the data values from one or more subjects, or groups, or populations can be received, stored, accumulated, processed, or used on one or more servers 920 operated centrally (e.g., in the "cloud") and the data values or the results of such activities can be made available from the cloud to users 922 through web browsers 924 anywhere. For example, real time or archived data values or characterizations can be used by clinicians to make decisions about and study diagnosis, prognosis, and therapy. Patient data values can be collected and stored locally or in the cloud. Functional changes in muscles or nerves, for example, can be monitored and used in determining required modification of configurations or assistive technology setup and in controlling remote configuration of assistive technology.

Monitoring can be used for applications in which muscle contractions, gestures, or intent are tracked and mapped to a physics-based model of the motion of the hand or another part of a body. The use of the physics-based model can enhance the quality of the characterizations derived by the processor by enabling correction of the characterizations based on constraints implied by the models. For instance, if someone extends his finger, the model constraints wouldn't allow this gesture characterization to move the finger beyond that which is capable of the joint and musculature connected to the finger.

Another broad area of applications involves control of a device or process based on the data values or characterizations (e.g., gestures or intent) derived by the technology.

In a simple but useful application, control can involve using characterization information to control an onscreen avatar using finger motions.

The control can be control of mobile devices, for example. In the medical realm, control can enable a patient to use gestures and intent to control the operation or state of a mobility device, including control of a car, a wheelchair, personal robotics, controllable orthoses.

Control can include control of a household environment or a component or element of such an environment, such as elevators, windows, doors, curtains, blinds, thermostats, heating and air conditioning devices, electrical sockets, intercoms, door lock releases, sump pumps, lights, alarms and other security devices, media devices, cleaning and cooking devices, bathing and other bathroom equipment, entertainment devices including televisions, media centers, video games, game devices, DVDs, telephone and other communication equipment, and emergency call recordings to be played back on a telephone, among others.

In some implementations, control can be control of devices in contexts of safety, security, silence, privacy, policing, and intelligence. Gestures or intent of a user derived as one or more characterizations based on detected electrical potentials could be used, for example, to trigger a silent alarm for help or to alert another party of a danger; to trigger an emergency call, such as by an avalanche victim, by a bank employee in the context of a robbery, or by military or police personnel to control military or policing devices silently or remotely.

Control applications include those for controlling functions of game controllers, joysticks, or other virtual reality control devices including augmented reality glasses, for example, in an industrial setting. Other control applications include navigating menu selections of a user interface. In some cases, a user could be holding something in her hands and also be using gestures to control an interface being presented by augmented reality glasses. In some cases, a person could be walking along a course indicated on a map in augmented reality glasses and could use gestures to control the interface. In some applications control could be asserted by gestures within a space suit.

In general, the technology can be especially useful in situations in which the ability of the user to perform full gestures is constrained, such as in a space suit, or a SCUBA suit, or when the user's hands or other parts of his body are occupied in other ways and therefore cannot be used to perform normal gestures.

In some instances, a user could control a virtual reality or augmented reality avatar.

A substantial range of applications involve interaction between user interface devices (such as a wrist device) and features of applications such as smart glasses. For example, the HMI can pass characterization information to the smart glasses (or other head-worn displays) to implement hands-free, voice-free control. For instance, augmented reality systems for pharmaceutical clean rooms can be provided with characterizations of user gestures or intent to control production, quality control, packaging, and other functions in the manufacturing of pharmaceuticals. In such contexts, users often are performing complex tasks and do not have free hands to control the augmented reality display. In addition, such environments may be noisy or multiple people are present, making voice control not viable.

In some implementations, for example, as shown in FIG. 18, user interface devices (such as a wrist device) 950 can detect motions of the hand 952, wrist 954, or fingers 956, for example, made by a user to express gestures (or intent). An HMI 958 can include a translation component 961 that executes an algorithm to translate the detected motions into control of one or more displayed elements 960 of a displayed user interface 962 of an application 964.

Among the motions of the hand, wrist, or fingers that could be detected are (in aviation terms) yawing or pitching or rolling of the hand or wrist or both or combinations of yawing, pitching, or rolling or a variety of other motions of the hand, wrist, or fingers (together called the "hand/wrist/finger motions"). Among other things, the user can twist or rotate 966 his hand (often in combination with twisting or rotation of his wrist) about an axis 968 generally aligned with the length of the user's forearm. The hand/wrist/finger motions can be interpreted as one or more actions, gestures, or intentions meant to control the displayed elements 960.

The displayed elements could be a cursor, or an insertion point, or a graphical element such as a sphere, or a character such as a cartoon figure or an avatar.

In some cases, the hand/wrist/finger motions could include twisting or rotation of the hand and wrist, the displayed element could include a sphere or some representation analogous to a sphere 960, and the twisting or rotation can be translated to a corresponding rotation or other motion of the sphere relative to the displayed user interface. By manipulating the sphere a user can in effect use the sphere for interacting with the displayed user interface, for example, to point to other displayed elements, move the elements, select actions, perform actions, and other activities. More generally, the hand/wrist/finger motions can be used to control any controllable aspect of an application through its displayed user interface, such as menus, content entry, gaming elements, interaction with other users, or navigation through a two-dimensional or three-dimensional displayed space, among other things.

The translation component 961 of the HMI 958 can include a mapping algorithm 968 that translates signals 970 representing the hand/wrist/finger motions to corresponding directions, orientations, rates of motion, or magnitude of motion (or combinations of them) of the displayed element, enabling the user to use gestures to control the displayed element.

In some examples, the direction, orientation, rate, and magnitude of twisting or rotation of the user's hand can be translated into proportional motion of the sphere or other displayed element having corresponding direction, orientation, rate of motion, and magnitude. In some cases, one or more of the direction, orientation, rate of motion, and extent of motion of the displayed element can be other than a direct proportional mapping from the hand/wrist/finger motions. The mapping can have any degree of simplicity or complexity.

One useful mapping algorithm can translate the magnitude of motion of the hand and wrist into a proportionately larger magnitude of motion of the sphere or other displayed element. For example, a 5 degree rotation of the hand and wrist could translate to a 20 degree rotation of the sphere, representing an amplification factor of the algorithm. The amplification factor could change dynamically with one or more features of the hand/wrist/finger motions such as magnitude or acceleration or both. For example, a small, fast rotation of the hand and wrist could be translated to a large rotation of the sphere. Conversely, slow acceleration of the hand and wrist could be translated using a relatively low amplification factor.

In some examples, motions of the wrist including rotation or panning or both could be used to control a rotary dial to choose among a set of icons arranged at respective angular positions relative to the rotary dial. The wrist motions could be translated one-to-one such that a 45-degree rotation translates to a corresponding 45-degree rotation in a rotary or linear array. Or small motions could translate to larger motions through amplification as noted above.

Communication between the wrist device and smart glasses can also be used for application switching (e.g., object oriented application switching).

With respect to feedback, the technologies that we have described have applications in contexts in which providing feedback about detected electrical potentials, or characterizations derived from them (e.g., muscle contractions, gestures, intent), can be useful for improving conduct, behavior, accuracy, or precision of gestures or intent or muscle contraction. Feedback could include visual, audible, haptic, or other modes of presentation to a user. Feedback could occur in real time or later. The feedback can directly present (say visually or audibly) an actual gesture, intent, or muscle contraction back to the user in real time to enable the user to immediately and directly alter an attempted gesture, intent, or muscle contraction to tend toward an ideal. In some cases, the feedback can present information that indirectly implies to the user how changes in attempted muscle contractions, gestures, or intent could more accurately, precisely, or usefully serve a goal or purpose.

Haptic feedback can be presented to the sense of touch of the user, for example, by vibrating or otherwise moving a smart phone or a wrist device or another device with respect to the skin of the user. Haptic feedback can improve control or triggering actions of a user. In some cases, haptic feedback can help in retraining muscles in patients with paresis (by improving neuroplasticity). To accomplish this, patients would be provided with a physical therapy activity or regime where the device would recognize the completion of the action or gesture responding with a haptic cue that it was performed correctly. It then becomes a training exercise with very clear and prompt cues based on the user's own interactions with the device.

In some instances, haptic feedback could provide cues as a non-visible, non-auditory interface to enable a user to, for example, navigate through menus of an application using a haptic vocabulary. More generally, haptic feedback can use a haptic vocabulary (in which the user can be trained) to provide a simple, discreet, non-visible, non-auditory technique for informing a user about a state or condition or change in a process, device, or application that can be achieved by a corresponding muscle contraction, gesture, or intent of the user that yields detectable tissue electrical signals.

In some cases, feedback can be visual using lights, displays, or other visual devices and cues. For example, the feedback can be used to provide visualization cues about actual electrical potentials, data values, muscle contractions or relaxations, gestures, or intent. The visual devices and cues can be presented on a user interface of a smart watch or wrist device, on a smart phone, or on an application such as smart glasses.

Feedback can be of any kind that aids actuation or control of one or more features of a virtual reality or augmented reality or an interface or device through which a virtual reality or augmented reality is presented. For example, a user can move his fingers using the wrist device described above to control a drone moving through a virtual reality world or through the real world. Thus, the feedback can be useful in military applications in which augmented or virtual realities are being presented, or in a medical context in which a display screen presents an augmented reality view of a hidden site at which a procedure is being performed.

In general, feedback can provide contextual, intuitive, application-specific switching and control of application devices and processes.

Some applications of the technologies are in the broad field of communication and enable users to communicate based on muscle contractions and relaxations, gestures, intent, or other characterizations. For example, such a user can cause such characterizations to cause typing of characters into a word processing application, text into a texting application, moving a mouse, engaging in alternative or augmentative communication, sending Morse code, and communicating in multiple channels in parallel, e.g., by both talking and moving fingers, or using eye movements and hand movements at the same time through distinct communication channels. In covert applications, control or communication could be done by a user by gestures of his hand in his pocket, hidden from view. Hidden gestures can be used for phone control, clandestine communication, prosthetics and exoskeletons, or keyboard or mouse replacement.

Some applications can involve receiving, collecting, and analyzing data values generated by the technology. For example, in implementations that use machine learning techniques for deriving characterizations from data values, it can be useful to collect and analyze data values for a single user as a means, for example, of training a classifier to classify future data values based on feature sets among various gestures or intent. Collecting and analyzing data values for groups or populations of thousands or millions of users can enable the generation of useful templates (feature sets) for later classification for any user. In some applications, data values combined with knowledge of the corresponding orientation and position of the user interface device, such as a wrist device, enables determining advantageous orientations and positions for the electrodes of other user interface devices, for example, orientations and positions at which tissue electrical signals are particularly robust or can be effectively detected and processed.

As mentioned above, some applications involve control of and communication with smart glasses. The gesture vocabulary for controlling or communicating with smart glasses could include: (1) entering into a "listen" mode by moving two fingers at the same time (2) subsequently rotating the wrist to navigate through a circular selection menu of, say, three or more items. (3) subsequently moving fingers to make the selection or releasing the held "listen" movement to make the selection. Typing into the user interface can be done using gestures to navigate through groupings of letters, for example.

In general, in applying the technology, a vocabulary of characterizations can be established and correlated with particular feature sets of the data values. Once a vocabulary has been established, the vocabulary can be used for a wide variety of purposes with respect to applications, just as any language vocabulary can be used. The vocabulary can be altered, updated, and enhanced as needed both by developers and by users. The correlation between data values and elements of the vocabulary can be updated, enhanced, and improved. The HMI platform or the user interface device or both can maintain and implement such a vocabulary and serve in effect as a translator between data values and elements of the vocabulary; then applications can use communications that are phrased according to the vocabulary in a wide variety of ways. Such a vocabulary can be implemented silently without requiring speech or (in some cases) actual motion of any part of the user's body. In this way, a user's intentions can be used to express communications based on the vocabulary. Such a vocabulary can be specific to a user or to a group or to a general population.

The text below (and in some cases earlier) includes certain text or information from the provisional application (U.S. patent application 62/429,334, filed Dec. 2, 2016) with respect to which this application is entitled to the priority of the filing date. (The entire provisional application is incorporated here by reference.)

The capability of measuring electrical signals in nerves has various uses, for example, helping people with Amyotrophic Lateral Sclerosis (ALS), ALS is a disease in which the neurons that control voluntary muscles degenerate and die. Its causes are not fully known or understood, although some incidents are attributed to genetics. A person with ALS will experience muscle stiffness, cramping, twitching, and weakness as neurons are lost and the muscles atrophy. Communication becomes difficult. Eventually, the person may lose muscle control needed for speech, for eating, and even for breathing.

Surface Electromyography (sEMG) is a form of electromyography that measures electrical activity in a muscle using sensors (electrodes) placed on the skin surface above the muscle. Two or more such electrodes can be used to measure electric potential (voltage) differences between distinct electrodes. Using these electrodes, an electromyograph can detect the electric potential generated by the muscle cells when activated by neurological (or electrical) signals. sEMG is less invasive than other forms of electromyography that require subcutaneous sensors.

Electroneurograms (ENGs) provide visualizations of electrical activity of neurons based on electrical signals obtained directly from electrodes placed into the neuron tissue. The electrical signals provided by the electrodes capture action potentials, which are potentials that rise and fall quickly. For example, when the brain sends a signal through a nerve to neurons in the vicinity of a muscle, the signal typically takes the form of an action potential.

Some rudimentary solutions exist to help a person with Amyotrophic Lateral Sclerosis (ALS) communicate with others, such as tracking eye gaze, but these solutions can be exhausting and difficult to use. For example, only about 10% of people with ALS can even use the eye gaze method. As described herein, surface electromyography (sEMG) can be used to control electrical equipment such as wheelchairs, remote control doors, entertainment systems (e.g., radios and televisions), and computer systems. This new level of control can more effectively and efficiently facilitate communication than existing technologies and will improve the over-all quality of life for persons with ALS.

A person with healthy muscles has surface electromyography (sEMG) measurable signals around 1 to 2 millivolts (i.e., 0.001 to 0.002 volts). People with Amyotrophic Lateral Sclerosis (ALS) can have compromised nerves and atrophied muscles such that the strength of their measurable signals could be in the 5-10 microvolt range, two hundred times smaller than a person with healthy muscles. Existing technology that uses sEMG, e.g., prosthetics control, require healthy muscle and nerve signals in the millivolt range. Accordingly, these technologies don't translate well to people with ALS. However, even if a person with ALS has no ability to move, the residual nerves in their forearm, leg, and jaw may still generate electrical signals that can be detected with sEMG.

As described here, sEMG sensors are used to detect a person's nerve and muscle signals and used to interface with electronic devices, e.g., computers and computer-controlled equipment. Configurations are customizable and modular to accommodate the range of user abilities and preferences. Electromyography activation is painless, requires zero movement, and is adaptable to ALS progression. Compared to eye gaze, which less than 10% of people with ALS use due to physical and mental strain, these systems are designed for people with little or no movement ability in their entire body. Further, because some implementations do not require any physical movement or gestures by a user, a person with ALS can use these solutions even if they are fully immobilized.

Figure 1A:
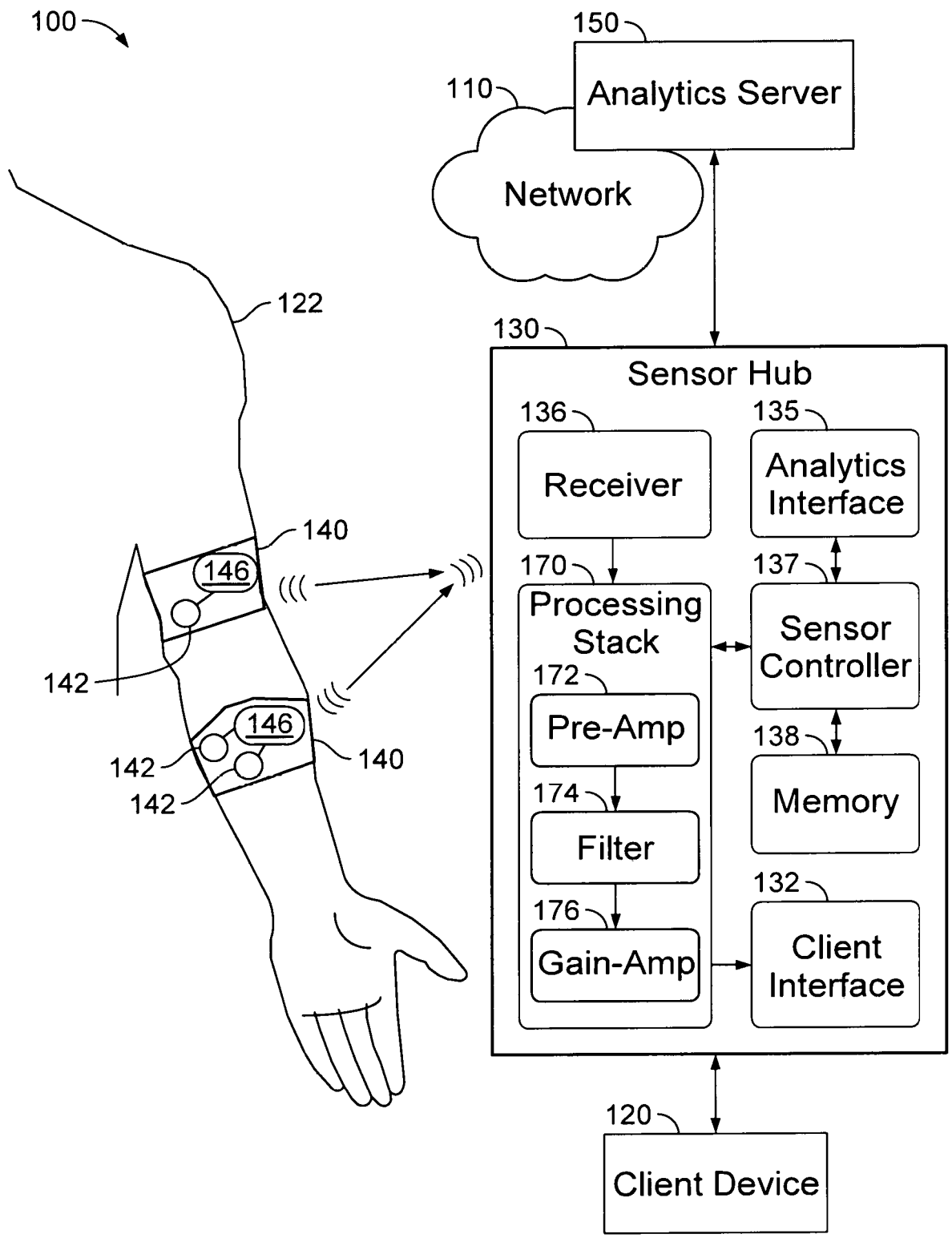
FIG. 1A is a diagram of an example sensor hub in communication with sEMG sensors and interfacing with a client device.
Figure 1B:
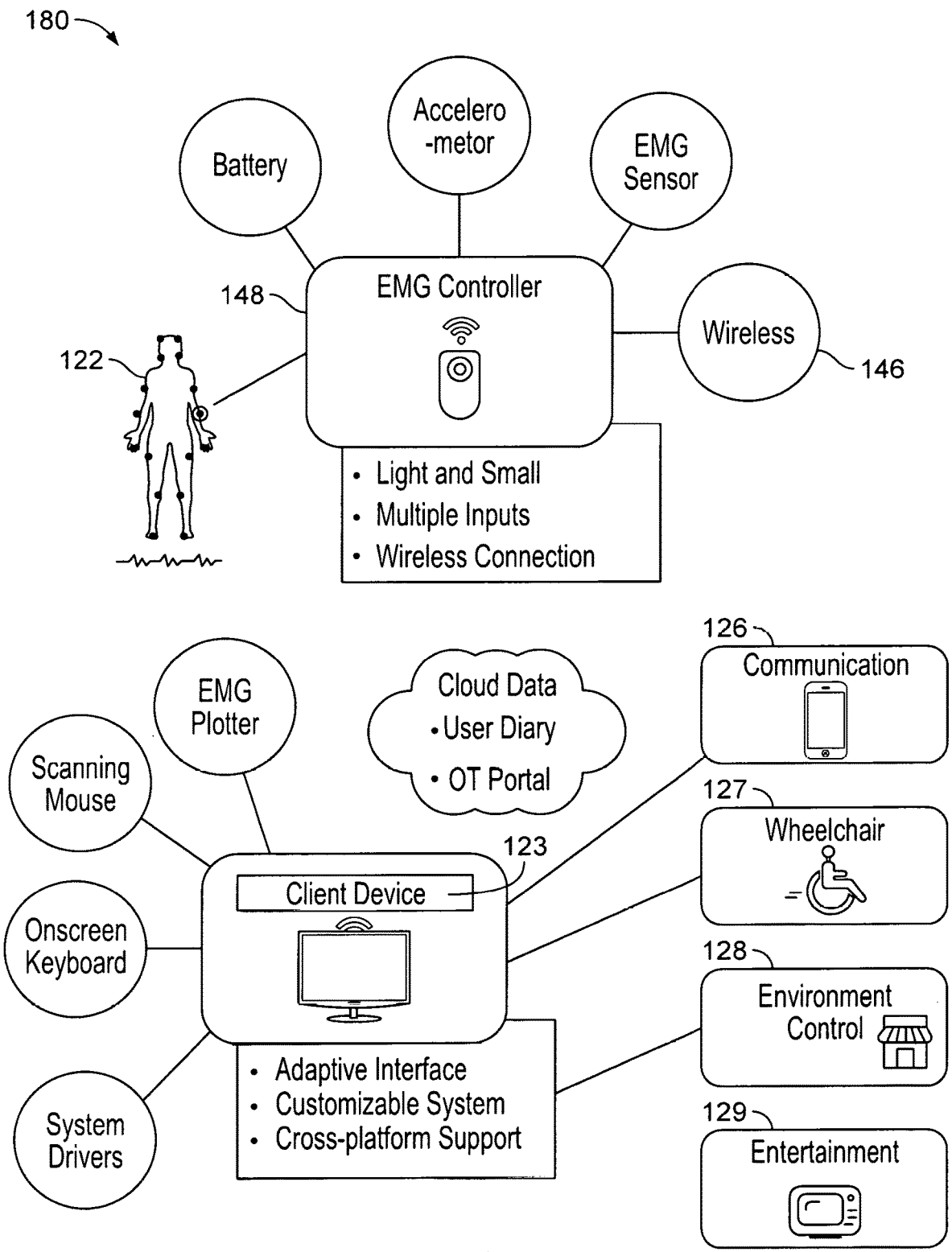
FIG. 1B is a diagram of a client device and an EMG controller.

FIG. 1 is a diagram of an example sensor hub 130 in communication with sEMG sensors 140 and interfacing with a client device 120 in an operation environment 100. In broad overview of the operation environment 100, a user 122 wears one or more sensor 140. Each sensor 140 includes one or more electrode patches 142 and a transmitter 146. The sensor transmitters 146 transmit data to a sensor hub 130. The sensor hub 130 includes a receiver 136 for receiving the data transmitted from the sensors 140. The sensor hub 130 includes a client interface 132, an analytics interface 135, a sensor controller 137, and memory 138. The sensor hub 130 includes a processing stack 170 that processes data received from the sensors 140 by amplifying and filtering received data. The illustrated processing stack 170 includes a pre-amplifier 172, a filter 174, and a gain-amplifier 176. The sensor hub 130 interacts with a client device 120 via the client interface 132. In some implementations, the sensor hub 130 sends data to an analytics server 150 via the analytics interface 135. The analytics interface 135 exchanges data with the analytics server 150 via a network 110. In some implementations, the client interface 132 also exchanges data with the client device 120 via the network 110.

Referring to FIG. 1 in more detail, each sEMG sensor 140 includes one or more electrode patches 142 and a transmitter 146. The sensors 140 also include a power source such as a rechargeable battery (not shown). An sEMG sensor 140 detects nerve activation in a person (e.g., a person with ALS), and provides data (e.g., a signal representative of a level of nerve activation) to the sensor hub 130. In some implementations, the sensor hub 130 is incorporated into a client device 120, such that the sensors 140 provide this data directly to the client device 120. In some implementations, multiple sEMG sensors 140 may be placed on a person, e.g., along a nerve path such as at the top of a forearm, middle of the forearm, and bottom of the forearm. In some implementations, the sEMG sensors 140 placed along a nerve path with detect the same activation event at slightly different moments in time; in some such implementations, the data is time shifted to align the signals such that they are coincident. This can help boost an activation signal above a noise level.

Each sEMG sensor 140 includes electrode patches 142 of electrodes that are placed either directly on the skin or very close to the skin, e.g., separated only by a thin film or layer of fabric (e.g., a conductive fabric). In some implementations, the sensors 140 are replaceable pads designed to adhere to the user 122 for a few hours, days, weeks, or months. In some implementations, the sensors 140 fit easily underneath clothing. In some implementations, the sensors 140 are wearable items where the components (e.g., the electrode patches 142 and transmitter 146) are packaged into straps, arm bands, watch bands, sweat bands, head bands, shirts, shorts, socks, or other items that can be worn on the body. In some implementations, wearable sensors 140 are designed for all-day ("24/7") wearability. Wearable sensors 140 may be designed for use in bed, in a wheelchair, outdoors, in a vehicle, and so forth. In some implementations, a wearable sensor 140 designed for use in bed can serve as an emergency alarm during sleep. The electrode patches 142 are oriented by the sEMG sensor 140 housing to place electrodes in direct contact with the skin of the user 122, or in near-direct contact with the skin, e.g., separated from the skin by only a thin film or layer of fabric. Each sEMG sensor 140 includes one or more electrode patches 142, and each electrode patch 142 includes one or more electrodes. To measure an electric potential (voltage) difference, at least two electrodes are needed. Medical grade electrodes are used. In some implementations, an electrode can be used for five or more days. In some implementations, the electrode patch 142 can be replaced in the sensor 140 without discarding the transmitter 146 or other components of the sensor 140.

In some implementations, each sEMG sensor 140 includes additional contextual and environmental monitoring elements such as thermometers, accelerometers, gyroscopes, barometers, and moisture or humidity sensors. Information from such elements is transmitted to the sensor hub 130 in the same manner as described with reference to the sEMG information from the electrode patches 142. The contextual and environmental monitoring information can be used to differentiate signal noise for nerve activation signals. Temperature shifts, humidity shifts, incidental movement, and other such contextual or environmental changes may be accommodated, for example, by adjusting how information from the sensor 140 is handled at the sensor hub 130.

Each sEMG sensor 140 includes a transmitter 146 to transmit data to a sensor hub 130. In some implementations, the transmitters 146 transmit an analog signal representative of the electric potential (voltage) difference measured from the electrodes in the electrode patches 142. In some implementations, the analog signal is amplified. In some implementations, the analog signal is broadcast using a frequency modulation or amplitude modulation of preconfigured radio frequencies. In some implementations, the transmitter encodes the analog signal into a digital signal, e.g., using an analog to digital (ATD) converter. In some such implementations, the digital signal is transmitted by the transmitters 146 in packet form, e.g., using a personal area network (PAN) protocol such as ANT+, BLUETOOTH, or ZIGBEE. Although illustrated in FIG. 1 as wireless, in some implementations, a sEMG sensor 140 does not communicate with the sensor hub 130 by radio and is, instead, configured to transmit data to the sensor hub 130 via a wired linkage.

The sensor hub 130 includes a receiver 136. The receiver 136 is an electrical circuit for receiving the data transmitted from the sensors 140. In some implementations, the receiver 136 is a radio receiver. In some implementations, the receiver 136 implements a personal area network (PAN) protocol such as ANT+, BLUETOOTH, or ZIGBEE. In some implementations, the receiver 136 is configured to receive signals from multiple sensor transmitters 146 concurrently. In some implementations, the receiver 136 is configured to receive signals from multiple sensor transmitters 146 using a time division multiplexing approach. In some implementations, the sensor hub 130 includes multiple receivers 136.

The sensor hub 130 includes a processing stack 170 that processes data received by the receiver 136 from the sensors 140. The processing stack 170 amplifies and filters received data. The illustrated processing stack 170 includes a pre-amplifier 172 ("pre-amp"), a filter 174, and a gain-amplifier 176 ("gain-amp"). In some implementations, the pre-amplifier 172 is a programmable operational high-gain electronic voltage amplifier ("op-amp") preamplifier. In some implementations, the finite bandwidth of the pre-amplifier 172 is configured to emphasize bandwidths specific to nerve activation signal levels of a person with ALS (in some implementations, this is an average range for people with ALS; in some implementations, this is tuned to a specific individual, e.g., an ALS patient). In some implementations, the pre-amplifier 172 can dynamically select thresholds above a noise floor. The amplified signal from the pre-amplifier 172 is then passed through one or more filters 174.

The filter 174 is a signal processing filter used to improve separation of input signals from the sensors 140 from general electronic noise. In some implementations, the filter 174 is an analog filter (e.g., an RLC filter); in some implementations, the filter 174 is a digital filter. In some implementations, the filter 174 is a high-pass filter, attenuating signals below a noise floor. In some implementations, the filter 174 is a band-pass filter tuned to a specific signal range. In some implementations, the filter 174 is configured to attenuate signals below and/or above a range specific to nerve activation signal levels of a person with ALS (in some implementations, this is an average range for people with ALS; in some implementations, this is tuned to a specific individual, e.g., an ALS patient). For example, a digital high-pass filter or digital band-pass filter can be tuned in this manner.

A gain-amplifier 176 boosts the strength of the filtered signal received from the filter 174. In some implementations, the gain-amplifier 176 is omitted. In some implementations, the processing stack 170 includes an analog-to-digital (ATD) converter that converts an analog signal from the gain-amplifier 176 (or directly from a filter 174) into a digital signal.

In some alternative implementations, some or all elements of the processing stack 170 are packaged in the sensor 146 and the output therefrom is transmitted to the receiver 136. Such alternative implementations are not shown in FIG. 1, but are considered to be within the scope of this disclosure.

The processing stack 170 provides the results of amplifying and filtering the received sensor input to the client device 120 via a client interface 132. In some implementations, the client interface 132 exchanges control messages with a control application executed at the client device 120. In some such implementations, the control application interprets the sensor data and converts the sensor data into control instructions at the client device 120. In some implementations, the client interface 132 interprets the sensor data and converts the sensor data into control instructions at the sensor hub 130. The instructions are then sent by the sensor hub 130 to the client device 120, e.g., via a physical or wireless network link.

The sensor hub 130 interacts with a client device 120 via the client interface 132. In some implementations, the sensor hub 130 sends data to an analytics server 150 via the analytics interface 135. The analytics interface 135 exchanges data with the analytics server 150 via a network 110. In some implementations, the client interface 132 also exchanges data with the client device 120 via the network 110. For example, in some implementations, the client interface 132 implements a BLUETOOTH communication channel with the client device 120.

In some implementations, the sensor hub 130 collects analytics information, e.g., information that may be used to improve the tuning of the sensor equipment and the processing stack 170. Analytics information is stored in memory 138 and/or transmitted to an analytics server 150 over a network 110. Analytics information may include, for example, measurements of metrics for daily usage, strength of signals for various nerve and muscle activations, and user patterns (which may be anonymized to protect patient privacy). All information is managed in compliance with the Health Insurance Portability and Accountability Act (HIPAA) and patient information is always protected. In some implementations, the analytics interface 135 exchanges messages with the analytics server 150 over a network 110, e.g., using a custom protocol layered over TCP. In some implementations, the analytics server 150 stores calibration and configuration information associated with a particular user 122. This allows the user 122 to use the same calibration and configuration information while using multiple implementations, e.g., at a diagnostic clinic, at home, at a hospital, and at other therapeutic centers. In some implementations, the analytics interface 135 receives updates from the analytics server 150. Updates may include, for example, refinements for tuning elements of the processing stack 170. This allows each sensor hub 130 to benefit from aggregate analysis of data from sEMG sensors 140 placed on a variety of people with ALS.

Still referring to FIG. 1, the memory 138 provides data storage for persisting data in the sensor hub 130. The memory 138 may be implemented using one or more data storage devices. The data storage devices may be any memory device suitable for storing computer readable data. The data storage devices may include a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, or BLU-RAY discs). Example implementations of suitable data storage devices include storage area networks (SAN), network attached storage (NAS), and redundant storage arrays.

The network 110 enables communication between network-connected devices. In some implementations, data flows through the network 110 from a source node to a destination node as a flow of data packets, e.g., in the form of data packets in accordance with the Open Systems Interconnection (OSI) layers. A flow of packets may use, for example, an OSI layer-4 transport protocol such as the User Datagram Protocol (UDP), the Transmission Control Protocol (TCP), or the Stream Control Transmission Protocol (SCTP), transmitted via the network 110 layered over an OSI layer-3 network protocol such as Internet Protocol (IP), e.g., IPv4 or IPv6. The network 110 is composed of various network devices linked together to form one or more communication paths between participating devices. Each networked device includes at least one network interface for receiving and/or transmitting data, typically as one or more data packets. An illustrative network 110 is the Internet; however, other networks may be used. The network 110 may be composed of multiple connected sub-networks. The network 110 can be a local-area network (LAN) such as a company intranet, a metropolitan area network (MAN), a wide area network (WAN), an inter network such as the Internet, or a peer-to-peer network, e.g., an ad hoc WiFi peer-to-peer network. The data links between devices in the network 110 may be any combination of wired links (e.g., fiber optic, mesh, coaxial, twisted-pair such as Cat-5 or Cat-6, etc.) and/or wireless links (e.g., radio, satellite, microwave, etc.). The network 110 may include carrier networks for mobile communication devices, e.g., networks implementing wireless communication protocols such as the Global System for Mobile Communications (GSM), Code Division Multiple Access (CDMA), Time Division Synchronous Code Division Multiple Access (TD SCDMA), Long-Term Evolution (LTE), or any other such protocol including, but not limited to, so-called generation "3G," "4G," and "5G" protocols. The network may include short-range wireless links, e.g., via Wi-Fi, ANT+, BLUETOOTH, or ZIGBEE, sometimes referred to as a personal area network (PAN) or mesh network. The network 110 may be public, private, or a combination of public and private networks. The network 110 may be any type and/or form of data network and/or communication network.

The example client device 120 is a computing system, or processor-based device, that executes applications, presents output to a user, and receives input from the user. The client device 120 is capable of receiving information from the sensor hub 130, e.g., via a direct wired link, via a wireless link (e.g., on a PAN), via an infrared link, via a network 110, or by other communication means. In some implementations, the client device 120 can be controlled by the sensor hub 130. The client device 120 may be any kind of computing device, including, for example, a desktop computer, a laptop or notepad computer, a mobile device such as a tablet or electronic pad, a personal digital assistant, a smart phone, a video phone, or an entertainment device such as a radio, a television, or any other such device. The client device 120 may be a robotic device such as a wheelchair, a remote control door, etc. In some implementations, the client device 120 includes one or more hardware elements for facilitating data input and data presentation, e.g., a keyboard, a display, a touch screen, a microphone, a speaker, and/or a haptic feedback device. In some implementations, the client device 120 is implemented using special purpose logic circuitry, e.g., an application specific integrated circuit (ASIC). In some implementations, the client device 120 is implemented using a system on a chip (SoC) semiconductor device that includes at least one processor (or microprocessor) core. In some implementations, the client device 120 is implemented using a general-purpose computing processor. FIG. 8, described in more detail below, illustrates a computing device that, in some configurations, is suitable for use as a client device 120.

Figure 2:
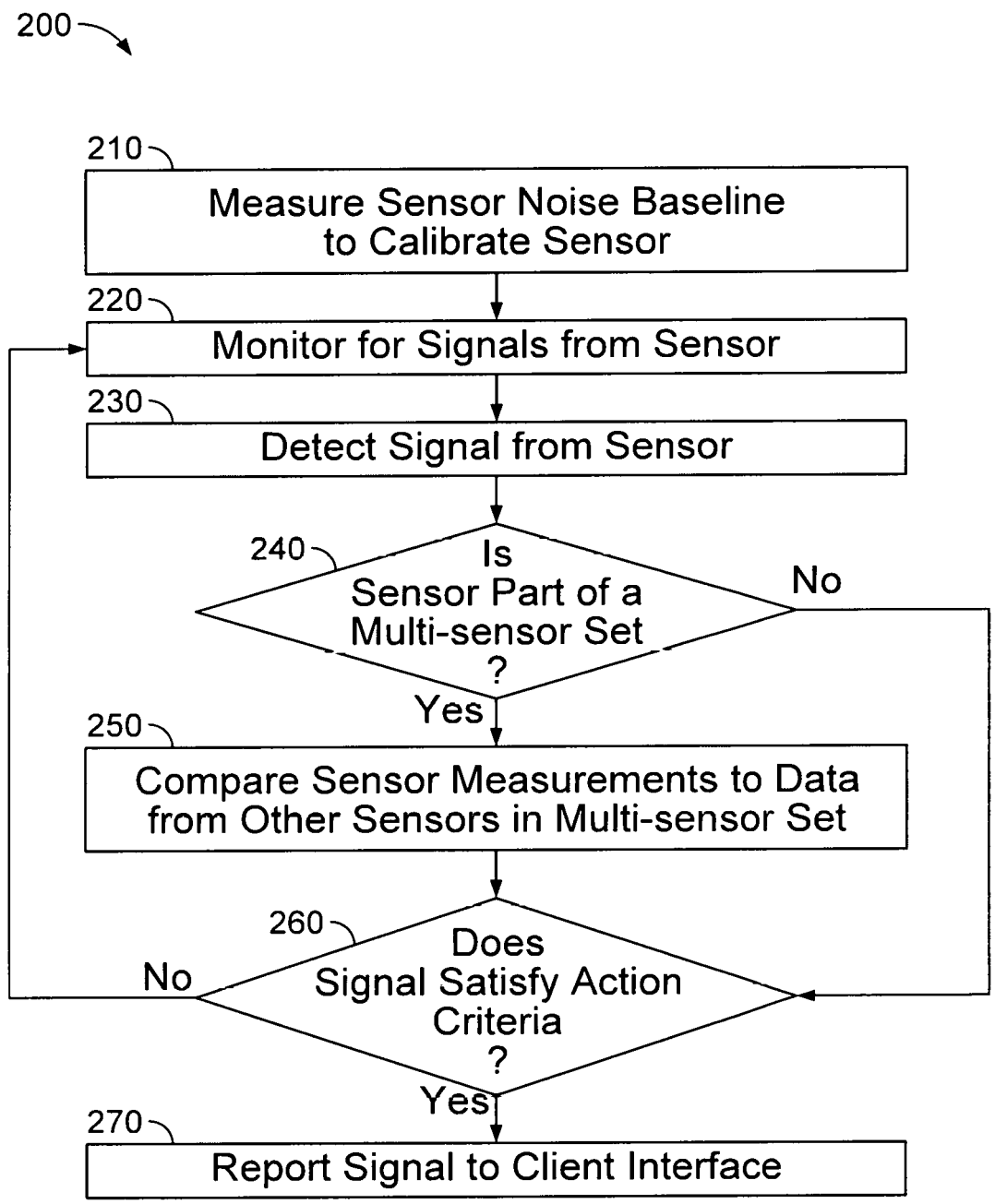
FIG. 2 is a flowchart for an example method of monitoring sEMG sensors.

FIG. 2 is a flowchart for an example method 200 of monitoring sEMG sensors. This description refers to a single sensor, but is applicable to one or more sensors, including groups or sets of sensors. This description allocates all monitoring and control tasks to the sensor controller 137; however, in some implementations, some or all of these tasks may be performed by the client interface 132 or by some other element in the sensor hub 130, on a sensor 140, or even at the client device 120. In broad overview, at stage 210, the sensor controller 137 calibrates a sensor 140. Calibration may be automated, e.g., by measuring sensor noise to establish a baseline. At stage 220, the sensor controller 137 monitors the sensor 140 for signals and, at stage 230, detects a signal from the sensor 140. If the sensor is part of a multi-sensor set (branch 240), then at stage 250, the sensor controller 137 compares sensor measurements from the detected signal to data from other sensors in the multi-sensor set. A true nerve activation signal may generate signals at multiple sensors in the set at various strengths and slightly different times (e.g., rippling through the sensors) such that analysis of the aggregate conditions can differentiate between the true nerve activation signal and general system noise. At stage 260, the sensor controller 137 determines if the detected signal satisfies action criteria. For example, determining whether the signal (or set of signals) exceeds a noise threshold or is sustained for a minimum length of time. If so, then at stage 270 the sensor controller 137 reports the signal to the client interface 132. The client interface 132 can then issue a control message to the client device 120, or report the signal to the client device 120, which can then determine the appropriate action.

Referring to FIG. 2 in more detail, at stage 210, the sensor controller 137 calibrates a sensor 140. Calibration may be automated, e.g., by measuring sensor noise to establish a baseline. In some implementations, a user 122 may wear the sensor 140 and trigger (or have an aide trigger) the calibration process while remaining passive. The sensor 140 gathers information about the baseline passive state, e.g., sEMG levels and contextual noise information. In some implementations, calibration is fully automatic. In some implementations, calibration includes manual adjustments or configurations. For example, the user 122 may be asked to activate various nerves and the sensor 140 can be further calibrated based on the sensitivity needed to detect the nerve activations. In some implementations, calibration is occasionally or periodically repeated.

At stage 220, the sensor controller 137 monitors the sensor 140 for signals. In some implementations, the sensor 140 is constantly (or periodically) reporting sensor status information. The sensor hub 130 receives this status information from the sensor 140 and monitors it for actionable conditions.

At stage 230, the sensor controller 137 detects a signal from the sensor 140. When a signal arrives from the sensor 140 that exceeds the baseline, the sensor controller 137 attempts to classify the signal as either intermittent noise or an actionable signal.

If the sensor is part of a multi-sensor set (branch 240), then at stage 250, the sensor controller 137 compares sensor measurements from the detected signal to data from other sensors in the multi-sensor set. A true nerve activation signal may generate signals at multiple sensors in the set at various strengths and slightly different times (e.g., rippling through the sensors) such that analysis of the aggregate conditions can differentiate between the true nerve activation signal and general system noise.

At stage 260, the sensor controller 137 determines if the detected signal satisfies action criteria. For example, determining whether the signal (or set of signals) exceeds a noise threshold or is sustained for a minimum length of time.

If the sensor controller 137 determines that the detected signal satisfies the action criteria, at stage 270, the sensor controller 137 reports the signal to the client interface 132. The client interface 132 can then issue a control message to the client device 120, or report the signal to the client device 120, which can then determine the appropriate action.

FIG. 3A, FIG. 3B, and FIG. 3C are screen images for an example implementation of a sensor monitor and interface. Flowcharts for interactions shown in FIG. 3A, FIG. 3B, and FIG. 3C are described in more detail below.

In broad overview, FIG. 3A depicts selection of an icon using a pointer or mouse-based interaction. As will be described, a vertical bar 310 and a horizontal bar 320 are manipulated by repeated input signals. The vertical bar 310 passes through a selected coordinate on a display's X axis and the horizontal bar 320 passes through a selected coordinate on the display's Y axis. The vertical bar 310 and horizontal bar 320 are manipulated to intersect at the selected X and Y coordinates. For example, as described below in reference to FIG. 5, the vertical bar 310 can be moved horizontally in a horizontal scan and the horizontal bar 320 can be moved vertically in a vertical scan. An icon 330 at the resulting [X,Y] intersection can then be selected, e.g., to open a corresponding application.

FIG. 3B depicts text entry into an input field 340 using a virtual keyboard 350. In some implementations, the virtual keyboard 350 is a reproduction a numeric or telephone key layout. In some implementations, the virtual keyboard 350 is a set of directional arrows. In some implementations, the virtual keyboard 350 is a reproduction of a standard "QWERTY" keyboard layout. In some implementations, the virtual keyboard 350 uses an alphabetical layout. In some implementations, the virtual keyboard 350 uses an alternative layout such as Dvorak or Colemak. In some implementations, the virtual keyboard 350 is fully customizable such that a user or operator can configure the virtual keyboard 350 for a particular user or use scenario. In some implementations, the virtual keyboard 350 includes buttons for custom macros or character sets. For example, buttons may be presented in the virtual keyboard 350 for emojis, common emoticons, or word suggestions. In some implementations, the virtual keyboard includes predictive buttons populated with word completion predictions, next word predictions, and/or frequently used words or phrases.

FIG. 3C depicts a row of virtual keys 360 (from the virtual keyboard 350) highlighted during a key selection process. A chart 370 provides a visualization of the signal strength for a sensor (or set of sensors) in use to select from the row of virtual keys 360. The screen images for the example implementation depicted in FIG. 3A, FIG. 3B, and FIG. 3C are referenced in the following flowchart descriptions. The examples shown in FIG. 3A, FIG. 3B, and FIG. 3C are from just one of many possible implementations, and are not meant to be limiting.

FIG. 4 is a flowchart for an example method 400 of selecting a matrix field using sEMG sensors. This description refers to a single sensor, but is applicable to one or more sensors, including groups or sets of sensors. This description allocates all tasks to the client interface 132; however, in some implementations, some or all of these tasks may be performed by some other element in the sensor hub 130, on a sensor 110, or even at the client device 120. The method 400 may be used to select from any matrix. For example, a key on a virtual keyboard (e.g., the virtual keyboard 350 shown in FIG. 3B) can be selected using the method 400. This description of FIG. 4 scans rows of the matrix before scanning columns of the matrix. In some implementations, columns of the matrix are scanned before rows of the matrix. In some implementations, a first set of sensors is used to scan rows and a separate set of sensors is used to scan columns; whichever set of sensors is triggered determines whether a row of the matrix is scanned or a column of the matrix is scanned. See, for example, FIG. 7 and the corresponding description below. These implementation variations and others are within the scope of this disclosure.

In broad overview of FIG. 4, at stage 410, the client interface 132 performs initialization functions to prepare for input selection. For example, the client interface 132 may request sensor recalibration, may present a selection matrix (e.g., a virtual keyboard) on a presentation screen (e.g., at the client device 120), and begin monitoring selection sensors. At stage 420, the client interface 132 receives notification of a signal from a sensor 140 and determines if the signal is sufficient to take action (see, e.g., method 200 illustrated in FIG. 2). If not (e.g., if the signal is too short), the client interface 132 returns to initialization stage 410 to wait for another signal.

Otherwise, if the signal is actionable, then at stage 430 the client interface 132 begins scanning rows of the selection matrix. The client interface 132 continues to scan rows of the selection matrix until signaled to stop. The last row scanned in stage 430 is identified as a selected row. At stage 440, the client interface 132 receives notification of a signal from a sensor 140 and determines if the signal is sufficient to transition to a next action. If not (e.g., if the signal is too short), the client interface 132 returns to initialization stage 410 to restart the method 400 and wait for another signal. At stage 440, the client interface 132 may also determine to return to stage 410 if too much time passes since starting stage 430. If, at stage 440, an actionable signal has been received, then at stage 450 the client interface 132 begins scanning columns of the selection matrix. The client interface 132 continues to scan columns of the selection matrix until signaled to stop. The last column scanned in stage 450 is identified as a selected column. At stage 460, the client interface 132 receives notification of a signal from a sensor 140 and determines if the signal is sufficient to transition to a next action. If not (e.g., if the signal is too short), the client interface 132 returns to scanning rows at stage 430 and waiting for another signal. At stage 460, the client interface 132 may also determine to return to stage 430 if too much time passes since starting stage 450. If, at stage 460, an actionable signal has been received, then at stage 470 the client interface 132 selects the matrix element at the intersection of the row identified in stage 430 and the column identified in stage 450.

Referring to FIG. 4 in more detail, at stage 410, the client interface 132 performs initialization functions to prepare for input selection. For example, the client interface 132 may request sensor recalibration, may present a selection matrix (e.g., a virtual keyboard) on a presentation screen (e.g., at the client device 120), and begin monitoring selection sensors.

At stage 420, the client interface 132 receives notification of a signal from a sensor 140 and determines if the signal is sufficient to take action (see, e.g., method 200 illustrated in FIG. 2). If not (e.g., if the signal is too short), the client interface 132 returns to initialization stage 410 to wait for another signal. This use of a discrete signal from one or more sensors for each action start, and for each action transition, allows a user 122 to rest between selections. In some implementations, timeouts are configured to allow for more or less rest as needed by a particular user 122. However, in some implementations, a user 122 may be expected to sustain a signal during an action, e.g., maintaining a selection signal while an event takes place.

If an actionable signal is received at stage 420, then at stage 430 the client interface 132 begins scanning rows of the selection matrix. The client interface 132 continues to scan rows of the selection matrix until signaled to stop. The last row scanned in stage 430 is identified as a selected row. For example, in FIG. 3C, a highlighted row 360 of virtual keys is shown selected.

At stage 440, the client interface 132 receives notification of a signal from a sensor 140 and determines if the signal is sufficient to transition to a next action. If not (e.g., if the signal is too short), the client interface 132 returns to initialization stage 410 to restart the method 400 and wait for another signal. At stage 440, the client interface 132 may also determine to return to stage 410 if too much time passes since starting stage 430.

If, at stage 440, an actionable signal has been received, then at stage 450 the client interface 132 begins scanning columns of the selection matrix. The client interface 132 continues to scan columns of the selection matrix until signaled to stop. The last column scanned in stage 450 is identified as a selected column. The scanning in stage 450 is similar to stage 430. The objective is to identify an intersection between a row and a column, which can then be selected. For example, to identify a key in a virtual keyboard 350.

At stage 460, the client interface 132 receives notification of a signal from a sensor 140 and determines if the signal is sufficient to transition to a next action. If not (e.g., if the signal is too short), the client interface 132 returns to scanning rows at stage 430 and waiting for another signal. At stage 460, the client interface 132 may also determine to return to stage 430 if too much time passes since starting stage 450.

If, at stage 460, an actionable signal has been received, then at stage 470 the client interface 132 selects the matrix element at the intersection of the row identified in stage 430 and the column identified in stage 450. For example, a single virtual key may be identified (see, e.g., the virtual keyboard 350 shown in FIG. 3B, in which a single key is highlighted). The selected key is then acted upon, e.g., entering a corresponding letter in a text entry field 340.

FIG. 5 is a flowchart for an example method 500 of operating a pointer using sEMG sensors. The method 500 is similar to the method 400 described in reference to FIG. 4, but differs in that the selection matrix is replaced by Cartesian coordinates or lines on a display. For example, as shown in FIG. 3A, scan lines 310 and 320 can be manipulated to intersect over a selectable element such as a graphical user interface (GUI) icon 330. Like the description of FIG. 4, this description of FIG. 5 refers to a single sensor, but is applicable to one or more sensors, including groups or sets of sensors. This description allocates all tasks to the client interface 132; however, in some implementations, some or all of these tasks may be performed by some other element in the sensor hub 130, on a sensor 140, or even at the client device 120. The method 500 identifies a Y axis coordinate with a vertical scan before identifying an X axis coordinate with a horizontal scan. In some implementations, horizontal scans are performed before vertical scans. In some implementations, a first set of sensors is used for vertical scans and a separate set of sensors is used for horizontal scans; whichever set of sensors is triggered determines whether a vertical or horizontal scan is performed. See, for example, FIG. 7 and the corresponding description below. These implementation variations and others are within the scope of this disclosure.

In broad overview of FIG. 5, at stage 510, the client interface 132 performs initialization functions to prepare for pointer or mouse input selection. At stage 520, the client interface 132 receives notification of a signal from a sensor 140 and determines if the signal is sufficient to take action (see, e.g., method 200 illustrated in FIG. 2). If not (e.g., if the signal is too short), the client interface 132 returns to initialization stage 510 to wait for another signal. Otherwise, if the signal is actionable, then at stage 530 the client interface 132 starts a vertical scan to identify a Y axis coordinate. The client interface 132 continues the vertical scan until signaled to stop. At stage 540, the client interface 132 receives notification of a signal from a sensor 140 and determines if the signal is sufficient to transition to a next action. If not (e.g., if the signal is too short), the client interface 132 returns to initialization stage 510 to restart the method 500 and wait for another signal. At stage 540, the client interface 132 may also determine to return to stage 510 if too much time passes since starting stage 530. If, at stage 540, an actionable signal has been received, then at stage 550 the client interface 132 starts a horizontal scan to identify an X axis coordinate. The client interface 132 continues the horizontal scan until signaled to stop. At stage 560, the client interface 132 receives notification of a signal from a sensor 140 and determines if the signal is sufficient to transition to a next action. If not (e.g., if the signal is too short), the client interface 132 returns to the vertical scan in stage 530 and waiting for another signal. At stage 560, the client interface 132 may also determine to return to stage 530 if too much time passes since starting stage 550. If, at stage 560, an actionable signal has been received, then at stage 570 the client interface 132 identifies and selects the intersection of the vertical identified in stage 530 and the horizontal identified in stage 550.

Referring to FIG. 5 in more detail, at stage 510, the client interface 132 performs initialization functions to prepare for pointer or mouse input selection. For example, like stage 410 in FIG. 4, the client interface 132 may request sensor recalibration, may present a horizontal scan line 320 (or vertical scan line 310) in an initial position on a presentation screen (e.g., at the client device 120), and may begin monitoring selection sensors. In some implementations, the client interface 132 switches between a mouse mode and a matrix mode (e.g., a virtual keyboard mode). In such implementations, the client interface 132 enters mouse mode in stage 510.

At stage 520, the client interface 132 receives notification of a signal from a sensor 140 and determines if the signal is sufficient to take action (see, e.g., method 200 illustrated in FIG. 2). If not (e.g., if the signal is too short), the client interface 132 returns to initialization stage 510 to wait for another signal. Otherwise, if the signal is actionable, then the client interface 132 proceeds to stage 530.

At stage 530 the client interface 132 performs a vertical scan to identify a Y axis coordinate. The client interface 132 continues the vertical scan until signaled to stop. In some implementations, during the vertical scan, the client interface 132 causes a horizontal scan line 320 to be drawn on the screen and, as the vertical scan progresses, the line is moved vertically up (or down) the screen. In some implementations, during the vertical scan, a value for the Y coordinate corresponding to the horizontal scan line 320 is displayed on the screen. In some implementations, the rate at which the horizontal scan line 320 is moved (or redrawn) can be configured. In some implementations, a user 122 can signal for the progression to speed up or slow down.

At stage 540, the client interface 132 receives notification of a signal from a sensor 140 and determines if the signal is sufficient to transition to a next action. If not (e.g., if the signal is too short), the client interface 132 returns to initialization stage 510 to restart the method 500 and wait for another signal. At stage 540, the client interface 132 may also determine to return to stage 510 if too much time passes since starting stage 530. If, at stage 540, an actionable signal has been received, then the client interface 132 proceeds to stage 550.

At stage 550 the client interface 132 performs a horizontal scan to identify a X axis coordinate. The client interface 132 continues the horizontal scan until signaled to stop. In some implementations, during the horizontal scan, the client interface 132 causes a vertical scan line 310 to be drawn on the screen and, as the horizontal scan progresses, the line is moved horizontally across the screen. In some implementations, during the horizontal scan, a value for the X coordinate corresponding to the vertical scan line 310 is displayed on the screen. In some implementations, the rate at which the vertical scan line 310 is moved (or redrawn) can be configured. In some implementations, a user 122 can signal for the progression to speed up or slow down.

At stage 560, the client interface 132 receives notification of a signal from a sensor 140 and determines if the signal is sufficient to transition to a next action. If not (e.g., if the signal is too short), the client interface 132 returns to the vertical scan in stage 530 and waiting for another signal. At stage 560, the client interface 132 may also determine to return to stage 530 if too much time passes since starting stage 550. If, at stage 560, an actionable signal has been received, then the client interface 132 proceeds to stage 570.

At stage 570 the client interface 132 identifies and selects the intersection of the Y axis identified in stage 530 and the X axis identified in stage 550. For example, referring to FIG. 3A, the scan lines 310 and 320 intersect at an actionable icon 330. At stage 570, the client interface 132 selects the icon 330 and thereby invokes an action associated with the icon 330. For example, the scan lines 310 and 320 may intersect over an application icon, a menu icon, a virtual button, or some other selectable or actionable element. In some implementations, a user 122 can trigger one or more sensors in a first set of sensors to cause a first action at the identified intersection, and can trigger one or more sensors in a second set of sensors to cause a second action at the identified intersection. For example, sensors on a user's left side may be used to indicate a "left click," and sensors on a user's right side may be used to indicate a "right click."

FIG. 6 is a flowchart for an example method 600 of selecting a menu option using sEMG sensors. In broad overview of the method 600, at stage 610, the client interface 132 presents a selectable menu option. For example, in some implementations, a row in a drop down menu is shown highlighted. In some implementations, a radio button or check box is shown selected. At the method 600 progresses, different menu options may be shown highlighted or selected. At stage 620, the client interface 132 receives notification of a signal from a sensor 140 and determines if the signal is sufficient to transition to a next action, e.g., accepting the menu selection or moving to another menu option. If, at stage 620, the client interface 132 determines that the signal from the sensor meets the criteria for selecting the menu option, then at stage 630, the client interface 132 invokes the selected menu option.

FIG. 7 is a flowchart for an example method 700 of differentiating multiple sEMG sensors. In some implementations, sensors 140 can be assigned to different selection groups. When the client interface 132 receives a signal from one (or more) sensors in a set of sensors associated with a specific action, the client interface 132 sends control messages to the client device 120 to invoke the specific action. For example, sensors placed on a user's 122 right arm may be used for one action, sensors placed on the user's 122 left arm may be used for another action, sensors placed on the user's 122 legs may be used for another action, and so on. Placing multiple sensors along nerve path, e.g., along the forearm, allows for multiple opportunities to detect a nerve activation. In some implementations, the different sensors along the nerve path may detect slight signal elevations at slightly different moments, as the signal propagates down the arm. Analysis of the set of sensors taken together allow for an action associated with the set of sensors. For people with more control over nerve activation, this can double or triple message throughput. For example, using a left arm signal for vertical motion and a right arm signal for horizontal motion would allow the methods 400 and 500 to quickly reach a selection state. Referring to FIG. 7 in broad overview, at stage 710, the client interface 132 receives a signal from one set of multiple possible sets of sensors. At stage 720, the client interface 132 determines if the signal was received from a sensor in a set associated with a specific action. If so, then at stage 730, the client interface 132 causes the specific action to be performed. Otherwise, at stage 740, a default action (or no action) is performed.

A person can control multiple electronics at the same time and maintain communication seamlessly across environments. The disclosed systems provide users with multiple inputs for efficient on-screen keyboard and mouse control. A person could wear 1, 2, 3, 4, 6, or more sensors anywhere on his or her body. For example, one sensor could activate a left mouse click while another activates a right mouse click. Previous solutions had typing speeds around 6 words per minute; the disclosed keyboard input solutions have facilitated input roughly three times faster. Web browsing is likewise simplified and accelerated. In some implementations, software executed on either the sensor hub 130 or client device 120 can automatically map the configuration of the sensors 140 and auto-calibrate for conditions such as movement, sweat, and pressure.

FIG. 8 is a block diagram illustrating a general architecture of a computing system 101 suitable for use in some implementations described herein The example computing system 101 includes one or more processors 107 in communication, via a bus 105, with one or more network interfaces 111 (in communication with a network 110), I/O interfaces 102 (for interacting with a user or administrator), and memory 106. The processor 107 incorporates, or is directly connected to, additional cache memory 109. In some uses, additional components are in communication with the computing system 101 via a peripheral interface 103. In some uses, such as in a server context, there is no I/O interface 102 or the I/O interface 102 is not used. In some uses, the I/O interface 102 supports an input device 104 and/or an output device 108. In some uses, the input device 104 and the output device 108 use the same hardware, for example, as in a touch screen. In some uses, the computing system 101 is stand-alone and does not interact with a network 110 and might not have a network interface 111.

The processor 107 may be any logic circuitry that processes instructions, e.g., instructions fetched from the memory 106 or cache 109. In many implementations, the processor 107 is a microprocessor unit. The processor 107 may be any processor capable of operating as described herein. The processor 107 may be a single core or multi-core processor. The processor 107 may be multiple processors. In some implementations, the processor 107 is augmented with a co-processor, e.g., a math co-processor or a graphics co-processor.

The I/O interface 102 may support a wide variety of devices. Examples of an input device 104 include a keyboard, mouse, touch or track pad, trackball, microphone, touch screen, or drawing tablet. Example of an output device 108 include a video display, touch screen, refreshable Braille display, speaker, inkjet printer, laser printer, or 3D printer. In some implementations, an input device 104 and/or output device 108 may function as a peripheral device connected via a peripheral interface 103.

A peripheral interface 103 supports connection of additional peripheral devices to the computing system 101. The peripheral devices may be connected physically, as in a universal serial bus ("USB") device, or wirelessly, as in a BLUETOOTH™ device. Examples of peripherals include keyboards, pointing devices, display devices, audio devices, hubs, printers, media reading devices, storage devices, hardware accelerators, sound processors, graphics processors, antennas, signal receivers, measurement devices, and data conversion devices. In some uses, peripherals include a network interface and connect with the computing system 101 via the network 110 and the network interface 111. For example, a printing device may be a network accessible printer.

The network 110 is any network, e.g., as shown and described above in reference to FIG. 1. Examples of networks include a local area network ("LAN"), a wide area network ("WAN"), an inter-network (e.g., the Internet), and peer-to-peer networks (e.g., ad hoc peer-to-peer networks). The network 110 may be composed of multiple connected sub-networks and/or autonomous systems. Any type and/or form of data network and/or communication network can be used for the network 110.

The memory 106 may each be implemented using one or more data storage devices. The data storage devices may be any memory device suitable for storing computer readable data. The data storage devices may include a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, or BLU-RAY discs). Example implementations of suitable data storage devices include storage area networks ("SAN"), network attached storage ("NAS"), and redundant storage arrays.

The cache 109 is a form of data storage device place on the same circuit strata as the processor 107 or in close proximity thereto. In some implementations, the cache 109 is a semiconductor memory device. The cache 109 may be include multiple layers of cache, e.g., L1, L2, and L3, where the first layer is closest to the processor 107 (e.g., on chip), and each subsequent layer is slightly further removed. Generally, cache 109 is a high-speed low-latency memory.

The computing system 101 can be any workstation, desktop computer, laptop or notebook computer, server, handheld computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some implementations, one or more devices are constructed to be similar to the computing system 101 of FIG. 8. In some implementations, multiple distinct devices interact to form, in the aggregate, a system similar to the computing system 101 of FIG. 8.

In some implementations, a server may be a virtual server, for example, a cloud-based server accessible via the network 110. A cloud-based server may be hosted by a third-party cloud service host. A server may be made up of multiple computer systems 101 sharing a location or distributed across multiple locations. The multiple computer systems 101 forming a server may communicate using the network 110. In some implementations, the multiple computer systems 101 forming a server communicate using a private network, e.g., a private backbone network distinct from a publicly-accessible network, or a virtual private network within a publicly-accessible network.

It should be understood that the systems and methods described above may be provided as instructions in one or more computer programs recorded on or in one or more articles of manufacture, e.g., computer-readable media. The article of manufacture may be a floppy disk, a hard disk, a CD-ROM, a flash memory card, a PROM, a RAM, a ROM, or a magnetic tape. In general, the computer programs may be implemented in any programming language, such as C, C++, C4, LISP, Perl, PROLOG, Python, Ruby, or in any byte code language such as JAVA. The software programs may be stored on or in one or more articles of manufacture as object code. The article of manufacture stores this data in a non-transitory form.

While this specification contains many specific implementation details, these descriptions are of features specific to various particular implementations and should not be construed as limiting. Certain features described in the context of separate implementations can also be implemented in a unified combination. Additionally, many features described in the context of a single implementation can also be implemented separately or in various sub-combinations. Similarly, while operations are depicted in the figures in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all implementations, and it should be understood that the described program components and systems can generally be integrated in a single software product or packaged into multiple software products.

References to "or" may be construed as inclusive so that any terms described using "or" may indicate any of a single, more than one, and all of the described terms. Likewise, references to "and/or" may be construed as an explicit use of the inclusive "or." The labels "first," "second," "third," an so forth are not necessarily meant to indicate an ordering and are generally used merely as labels to distinguish between like or similar items or elements.

Having described certain implementations and embodiments of methods and systems, it will now become apparent to one of skill in the art that other embodiments incorporating the concepts of the disclosure may be used. Therefore, the disclosure should not be limited to certain implementations or embodiments, but rather should be limited only by the spirit and scope of the following claims.

Thus, some rudimentary solutions exist to help a person with Amyotrophic Lateral Sclerosis (ALS) communicate with others, such as tracking eye gaze, but these solutions can be exhausting and difficult to use. For example, only about 10% of people with ALS can even use the eye gaze method. As described herein, surface electromyography (sEMG) can be used to control electrical equipment such as wheelchairs, remote control doors, entertainment systems (e.g., radios and televisions), and computer systems. This new level of control can more effectively and efficiently facilitate communication than existing technologies and will improve the over-all quality of life for persons with ALS.

Other implementations are also within the scope of the following claims.

For example, although we have used the example of the wrist in much of our discussion, the technologies that we have described here can be applied in devices that measure electrical potentials on any other part of the body, including the feet, arms, legs, torso, and brain, for example.

Although we have discussed electrical signals appearing in muscles, bones, and nerves, it is possible that electrical signals may also appear in tendons, for example, because they may conduct or reflect electrical signals of muscles, for example, in a frequency range similar to the frequency range of muscle electrical signals. Our description related to electrical signals in muscles, nerves, and bones therefore may also apply to tendons.

What is claimed is:

1. A system comprising:
   detectors positioned at, and configured to detect electrical potentials at, a surface of a skin of a wrist of a hand of a user, wherein the detectors include a first pair of detectors configured to output a first output based on the detected electrical potentials and a second pair of detectors configured to output a second output based on the detected electrical potentials; and
   circuitry configured to:
      reduce amplitudes indicative of frequency components that are characteristic of ambient noise from the first output and the second output,
      obtain historical information representative of known relationships between (a) features of data values generated from the first and second outputs and (b) actions of particular muscles, gestures, or intent corresponding to the features of the data values,
      generate data values based upon the first output and the second output,
      extract features from the data values including at least a feature based on relative amplitudes between the first output and the second output,
      infer actions of particular muscles, gestures or intent of the user based on the historical information representative of the known relationships and the extracted features from the data values, and
      provide the actions to an application for use in controlling a user interface.

2. The system of claim 1, wherein the circuitry is further configured to provide additional data values representing motion of the wrist of the hand causing at least one of rolling, tilting, or yawing of the hand.

3. The system of claim 1, wherein the circuitry is further configured to provide additional data values representing at least one of rotating or twisting the wrist.

4. The system of claim 1, wherein the circuitry is further configured to provide additional data values representing direction, orientation, rate of motion, or magnitude of the motion of the wrist of the hand.

5. The system of claim 4, wherein the motion of the wrist of the hand corresponds to manipulation of a sphere.

6. The system of claim 4, wherein the motion of the wrist of the hand is associated with a motion of a displayed element of a displayed user interface of the application.

7. The system of claim 1, wherein the circuitry is further configured to provide the data values to the application for use in causing actions in the user interface.

8. The system of claim 7, wherein the actions in the user interface comprise selection of a menu item.

9. The system of claim 1, in which, wherein the circuitry is further configured to cause feedback to the wrist of the hand.

10. The system of claim 9, wherein the circuitry is further configured to cause haptic feedback to the wrist of the hand.

11. The system of claim 1, wherein the application is part of a camera.

12. The system of claim 1, wherein the application is part of smart glasses.

13. The system of claim 12, wherein the application that is part of the smart glasses comprises an application for control of at least one of production, quality control, or packaging in a manufacturing facility.

14. The system of claim 1, wherein the application comprises at least one of: menus, content entry, gaming elements, interaction with other users, or navigation through a two-dimensional or three-dimensional displayed space.

* * * * *